(12) United States Patent  (10) Patent No.: US 6,649,419 B1
Anderson                         (45) Date of Patent:     Nov. 18, 2003

(54) METHOD AND APPARATUS FOR PROTEIN MANIPULATION

(75) Inventor: N. Leigh Anderson, Washington, DC (US)

(73) Assignee: Large Scale Proteomics Corp., Germantown, MD (US)

( * ) Notice: Subject to any disclaimer, the term of this patent is extended or adjusted under 35 U.S.C. 154(b) by 247 days.

(21) Appl. No.: 09/722,405

(22) Filed: Nov. 28, 2000

(51) Int. Cl.[7] .............................................. G01N 33/53
(52) U.S. Cl. ...................... 436/526; 436/538; 436/535; 436/529; 436/541; 436/174; 436/177; 436/805; 436/806; 436/807; 436/514; 436/516; 204/182.8; 204/299; 435/7.1; 435/7.7; 435/286.7; 435/288.7; 435/288.6; 435/287.3; 435/287.2; 435/287.7; 435/287.9; 210/22; 210/416; 210/234; 210/232; 428/401; 530/412; 530/413
(58) Field of Search ................................. 436/526, 538, 436/535, 529, 541, 805, 174, 177, 806, 807, 514, 516; 204/182.8, 299; 435/7.1, 7.7, 286.7, 288.7, 287.3, 288.6, 287.2, 287.7, 287.9; 210/22, 416, 234, 232; 530/412, 413; 428/400

(56) References Cited

U.S. PATENT DOCUMENTS

| | | |
|---|---|---|
| 3,970,518 A | 7/1976 | Giaever ..................... 195/1.5 |
| 4,018,886 A | 4/1977 | Giaever ..................... 424/12 |
| 4,169,804 A | 10/1979 | Yapel, Jr. |
| 4,230,685 A | 10/1980 | Senyei et al. ................. 424/12 |
| 4,297,337 A | 10/1981 | Mansfield et al. ............. 424/1 |
| 4,452,773 A | 6/1984 | Molday ...................... 424/1.1 |
| 4,582,622 A | 4/1986 | Ikeda et al. .............. 252/62.53 |
| 4,628,037 A | 12/1986 | Chagnon et al. ............ 436/526 |
| 4,658,022 A * | 4/1987 | Knowles et al. |
| 4,701,419 A * | 10/1987 | Morris |
| 4,795,698 A * | 1/1989 | Owen et al. |
| 5,108,933 A | 4/1992 | Liberti et al. |
| 5,158,871 A | 10/1992 | Rossomando et al. ..... 435/7.32 |
| 5,395,498 A * | 3/1995 | Gombinsky et al. |
| 5,411,863 A * | 5/1995 | Miltenyi |
| 5,508,164 A | 4/1996 | Kausch et al. |
| 5,567,326 A | 10/1996 | Ekenberg et al. ........... 210/695 |
| 5,834,197 A | 11/1998 | Parton ........................... 435/6 |
| 6,103,537 A * | 8/2000 | Ullman et al. |
| 6,204,033 B1 * | 3/2001 | Muller-Schulte |
| 6,297,062 B1 | 10/2001 | Gombinski |
| 6,348,318 B1 * | 2/2002 | Valkirs |
| 6,387,628 B1 * | 5/2002 | Little et al. |
| 6,409,925 B1 * | 6/2002 | Gombinsky et al. |
| 6,448,092 B1 * | 9/2002 | Tuunanen |
| 6,455,325 B1 * | 9/2002 | Tajima |
| 6,468,432 B1 * | 10/2002 | Miltenyi et al. |
| 6,468,810 B1 * | 10/2002 | Korpela |

FOREIGN PATENT DOCUMENTS

| | | |
|---|---|---|
| EP | 1130397 | 9/2001 |
| WO | WO 00/01462 | 1/2000 |

\* cited by examiner

*Primary Examiner*—Christopher L. Chin
*Assistant Examiner*—Pensee T. Do
(74) *Attorney, Agent, or Firm*—John E. Tarcza; John C. Robbins

(57) ABSTRACT

A method and apparatus for extracting, identifying, and manipulating proteins or peptides from a solution uses paramagnetic beads having a coating with an affinity for the target component. In one embodiment, paramagnetic beads coated with C18 are used to adsorb proteins and peptides. The beads can be used to purify, immobilize and assay antibodies. By cycling the beads, many times greater molar amount of binding partner may be separated from a solution. A magnetic probe is used to capture the beads and transfer the beads to selected processing stages.

46 Claims, 12 Drawing Sheets

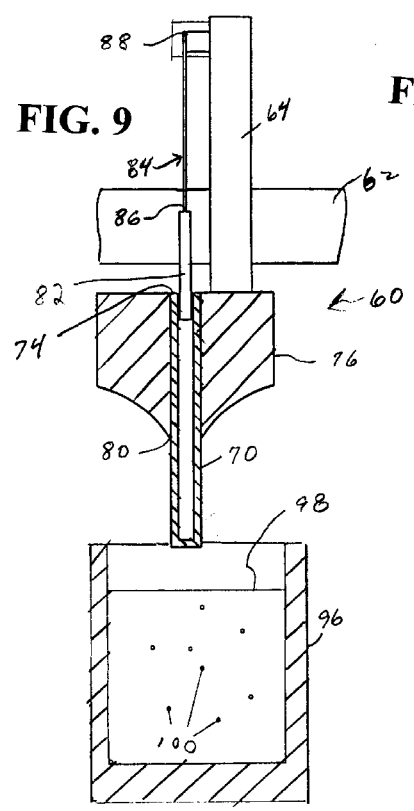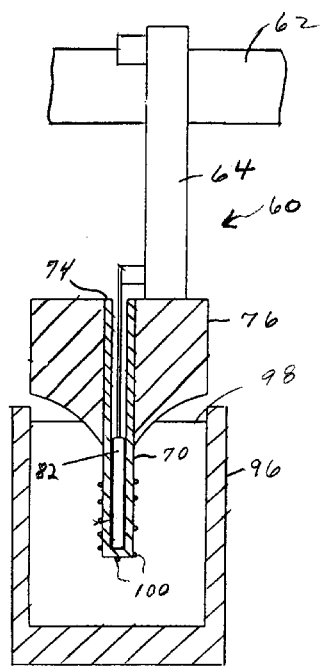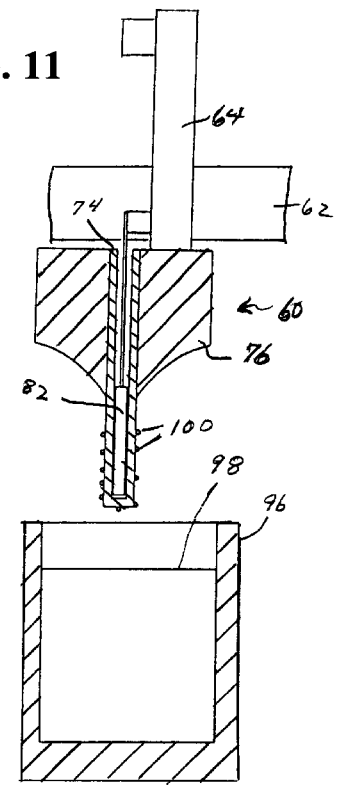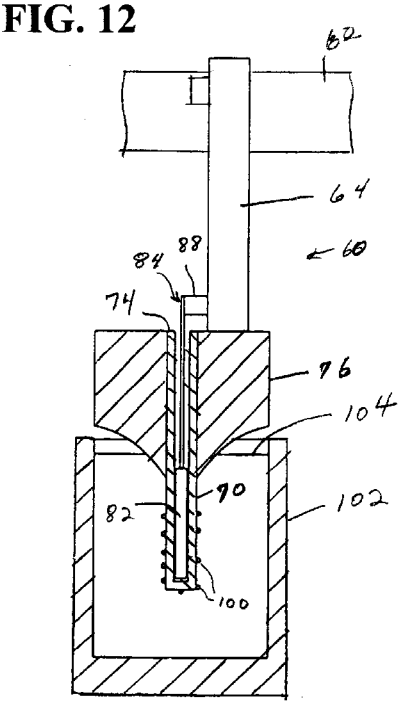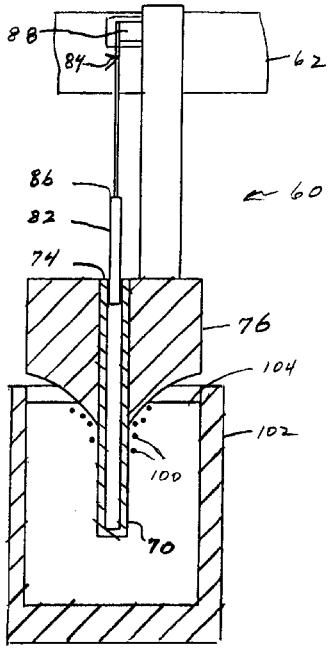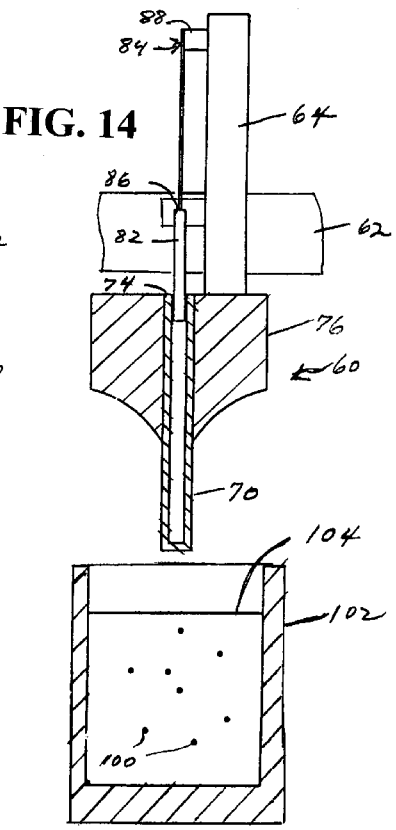

METHOD AND APPARATUS FOR PROTEIN MANIPULATION

FIELD OF THE INVENTION

The present invention relates to methods and apparatus for the manipulation of proteins and peptides by reversibly binding proteins and peptides to beads having a coating capable of binding with native proteins and peptides. More particularly, the invention is directed to methods and apparatus for capturing native proteins and peptides on magnetically responsive beads.

BACKGROUND OF THE INVENTION

Magnetically responsive beads or particles of small sizes are well known and have been used for a number of separation and diagnostic purposes. Small magnetic beads have been used to bind to cells and other particles in order to manipulate and separate them. See, for example, U.S. Pat. Nos. 4,230,685, 3,970,518, 5,508,164, 5,567,326 and 4,018,886.

Magnetic beads have been prepared from a variety of polymers with metal particles therein, including those prepared by gelatin, colloidal metal and other agents. An example of this type of bead is disclosed in U.S. Pat. No. 4,582,622. Chemical coupling of proteins to reactive moieties on magnetic beads has been proposed using various linking groups as disclosed in U.S. Pat. No. 4,628,037. While certain bonds may be cleavable, the protein binding is not disclosed as being reversible.

Magnetic beads coated with streptavidin have been used for immobilizing biotinylated substances. Magnetic beads of a polysaccharide (dextran) with a cleavable linker to protein A to immobilize antibodies and bind to a protein have been proposed in U.S. Pat. No. 4,452,773. Protein A coated magnetic beads have also been proposed in U.S. Pat. No. 5,158,871. U.S. Pat. No. 4,297,337 discloses magnetic beads made of porous glass.

U.S. Pat. No. 5,900,481 to Lough et al discloses using coated beads to bind to DNA and thereby manipulate the DNA. Other disclosures of manipulating various molecules bound to beads include Girault et al, Analytical Chemistry 68(13): 2122-6 (1996), and Tang et al, Nucleic Acids Research 23(16): 3126-31 (1995).

A number of magnetic separators for small beads are commercially available, which can readily remove micron size ferromagnetic particles from solution by employing relatively inexpensive permanent magnets. Examples of such magnetic separators include those manufactured by Ciba-Corning Medical Diagnostics, Wampole, Mass., the MAIA Magnetic Separator manufactured by Serono Diagnostics, Norwell, Mass., U.S.A., the DYNAL MPC-1 manufactured by DYNAL, Inc., Great Neck, N.Y., U.S.A., and the BioMag Separator, manufactured by Advanced Magnetics, Inc., Cambridge, Mass., U.S.A.

U.S. Pat. No. 5,834,197 to Parton discloses a method of capturing a species from a liquid using coated magnetic beads. The beads have a selective affinity for an antigen. A labeled antibody is added to sandwich the antigen and provide a detectable label bound to the magnetic beads for easy detection and recovery of the antigen.

One method for separation and purification of many different proteins in a sample is by using two-dimensional gel electrophoresis. Electrophoreses separation procedures are routinely applied to complex mixtures of proteins to resolve individual molecular species. Two-dimensional electrophoresis utilizes two orthogonal separations to produce a highly resolved pattern of protein spots, many of which may be effectively homogeneous protein samples. Examples include: O'Farrel, J. Biol. Chem. 250: 4007–4021, (1975), Anderson, et al, Anal. Biochem. 85: 3311–340, (1978), Anderson, et al, Anal. Biochem. 85: 341–354, (1978), Anderson, et al, Anal. Biochem. 93: 312–320, (1979) and Giometti, et, al, Anal. Biochem. 102: 47–58, (1980).

Methods have been described for the recovery of isolated proteins from such spots, generally for the purpose of characterization by microchemical Edman sequencing, amino acid analysis or mass spectrometry, or for preparation of an antigen for the immunization of animals to produce antisera.

It is current practice to identify an isolated protein found in these gels by excising a spot containing the protein of interest. Trypsin is added for cleaving the protein to generate peptides that are then identified by mass spectrometry (MS). One example is disclosed in Rosenfeld et al, Analytical Biochemistry 203:173–179 (1992). From the pattern of peptide molecular weights, or their fragments, one can then deduce the identity of the original protein by comparisons against a suitable sequence database.

One of the difficulties of this practice is that the quantity of these peptides is small and they diffuse freely from the gel into the surrounding liquid and interact with the walls of the container. The peptides in dilute solutions are recovered for use in MS analysis by centrifugal vacuum concentration (Speedvac system) or by lyophilization of a small volume of the surrounding liquid. This recovery step is fraught with difficulties, as the dilute peptides are exposed to plastic and other surfaces upon which they may be captured and thus lost to the investigator.

Likewise, when one wishes to isolate an intact protein from a spot on the gel, a recovery method is used. One method is electroelution, in which the protein is caused to move out of the excised gel spot under the influence of an electric field. In most procedures, the eluted protein is recovered in a small fluid volume by electrophoresing it against a membrane that is impermeable to protein of the expected molecular mass. Devices designed to accomplish this procedure are sold by BioRad, Pharmacia Biotech, Millipore and others. Such techniques suffer from low quantitative recovery probably due to the imperfect recovery of protein off the barrier membrane.

Other published procedures include adsorbing proteins into small C18 reverse phase chromatography columns for the HP G1000A protein sequencer. The Hewlett Packard protein sequencer may use sample cartridges that are small two-part disposable columns with an upper half containing C18 chromatography support, and a lower half containing an ion exchange support. As different aqueous and organic solvents flow through the cartridge, the direction of flow can be arranged so that the applied protein or peptide is always immobilized on the "downstream" support to prevent loss of material. It has been attempted to apply the protein to the C18 half of the column by electroeluting gel spot protein through the column. However, gas bubbles frequently form in the column and block the flow of current. Once successfully immobilized, the protein is then chemically modified and degraded for Edman sequencing directly.

Another technique is electroblotting, in which a gel is sandwiched against a protein-binding membrane, and an electric field is applied using suitable electrodes and buffers to cause the proteins to migrate out of the gel and through the membrane, where they are then immobilized. One, such example using a nitrocellulose blotting sheet is disclosed in Towbin, et al, Proc. Nat. Acad. Sci. USA 1979, 76, 4350–4354. The gel-separated proteins retain their spatial relationships while they move into the membrane, so that the pattern of separated proteins bound to the membrane is generally the same as the pattern of proteins resolved in the gel. When used with proteins this procedure is generally called "Western blotting". A drawback of the blotting approach is the difficulty of subsequently removing the blotted proteins from the membrane for subsequent manipulation in a different format.

Polyvinylidene difluoride (PVDF) is very hydrophobic and binds proteins well. Polyvinylidene difluoride membranes (Immobilon®, Milipore) have been used for recovery of proteins from two-dimensional gels and for using in situ digestion and transfer of peptides from two-dimensional gels. Kennedy et al, Proc. Natl. Acad. Sci. U.S.A. 85(18) :7008–12 (1988) and Kamps et al, Anal. Biochem, 176(1) :22–7 (1989). Membranes bearing charged groups have also been used (Millipore cationic membranes). In cases, where the resolved protein is small, or the gel medium has very large pores (as with agarose gels), it is possible to recover some of the protein by passive elution from the gel.

A common problem with the elution methods is that the protein solution is very dilute, not easily recovered in a small volume and in a form that is difficult to manipulate by robotic methods.

High-resolution t two-dimensional electrophoretic gels of human serum are also well known. Anderson, et al In: The Plasma Proteins, F. Putnam, ed., Academic Press, 2nd Ed., Vol. 4, pp 221–270, (1984).

Repeated adsorption and elution of antibodies wherein the immobilized antigen is used to eventually purify many times more of its specific antibody has been proposed. Anderson et al, Anal. Biochem. 66(1):159–74 (1975) and Anderson et al, Anal. Biochem. 68(2):371–93 (1975).

SUMMARY OF THE INVENTION

An object of the present invention is to provide small beads having a non-specific peptide-adsorptive surface, where beads can be readily manipulated for physical collection, movement and release by electromechanical means.

A further object of the present invention is to make and use small magnetically responsive beads having a reversible or irreversible attachment with a protein or peptide that in turn may be reversibly bound to an antibody or other receptor such that each reversible binding is elutable under different conditions than the protein or peptide to the bead.

Yet another object of the present invention is to provide a method and apparatus for the recovery and handling of proteins previously purified, such as those resolved as spots on 2-D electrophoretic gels by electroeluting protein from an excised gel spot through a bed of protein adsorbing beads.

Another object of the present invention is to attach an affinity label on a protein or peptide before purification or before separation from a permeable support material by reaction of the whole permeable support material containing the protein or peptide with reagents to link the affinity label to the protein or peptide.

In yet another embodiment, the affinity label bonded to the protein or peptide does not alter the net molecular charge and isoelectric point of the protein or peptide.

It is an object of the present invention to prepare proteins and peptides in a matrix for matrix assisted laser desorption ionization time-of-flight (MALDI-TOF) mass spectrometry or electrospray (ES) mass spectrometry, particularly for LC/MS/MS by elution from magnetically responsive beads.

It is still another object of the present invention to provide small amounts of antibodies having affinities to many specific proteins and to use bead immobilized proteins for affinity chromatography.

It is a further object of the present invention to prepare large amounts of antibodies and proteins from samples having low concentrations of the antibodies or proteins than can be prepared by analytical methods such as 2D electrophoresis or affinity capture in a single run.

It is another object of the present invention to provide a robotic assembly for manipulating magnetically responsive beads and to provide automated processing of many different proteins and antibodies, recovering the proteins or antibodies in parallel, and optionally identifying the proteins or associated components bound thereto in a complex.

It is another object of the present invention to provide a permanent magnet probe for the attraction and release of magnetically responsive beads where the magnet is moved within the probe to selectively attract and release the beads as a means to manipulate bound substances through plural reaction stations.

The present invention separates proteins by two-dimensional electrophoresis followed by excising a piece of gel containing a protein of interest, electro-eluting the protein of interest in a special apparatus, capturing the protein on magnetically responsive beads, manipulating the beads with a magnetic probe to wash, preferably by immersion, optionally renature, contact with antibody, elute the antibody, elute the protein, or analyze the protein for identification. Alternatively, the protein of interest is first cleaved and the peptides eluted and captured followed by washing and eluting directly onto a mass spectroscopy analyzer.

The invention accomplishes the manipulation of proteins and peptides in a manner where separation, purification, washing and elution occurs in large volumes of solution but the proteins or peptides being manipulated are quantitatively recoverable in small volumes of solution. The manipulation is performed by alternatively magnetizing and demagnetizing a probe after moving to another location.

The objects and advantages of the invention are basically attained by providing a magnetically responsive bead having a surface with an affinity binding member or a hydrophobic coating thereon. The coatings are capable of reversibly binding a protein or a peptide.

The objects of the invention also provide a coupling system for purifying a greater molar quantity of a binding partner which in turn may be cycled to purify a greater molar quantity of the original binding partner.

The foregoing objects and advantages of the invention are further attained by providing a bead composition comprising first magnetically responsive beads with a first coating having a binding affinity for immobilizing a first protein on the first beads; and second magnetically responsive beads with a second coating having a binding affinity for immobilizing a second protein on the second beads.

The foregoing objects and advantages of the invention are still further attained by providing a method of recovering proteins or peptides from a sample. The method comprises the steps of: providing a solution or dispersion of the sample; contacting the solution with an amount of magnetically responsive microbeads, and recovering the beads from the solution. The microbeads have an outer surface with a hydrophobic coating having a binding affinity for proteins or peptides. The microbeads are contacted with the solution for sufficient time to bind the proteins or peptides to the beads.

The foregoing objects and advantages of the invention are yet further attained by providing a method of recovering a target component from a solution comprising the steps of: providing an amount of magnetically responsive beads having a coating with a binding affinity for the target compound, contacting the beads with the solution for sufficient time to attach the target compound to the beads, separating the beads from the solution, and eluting the target component from the beads.

The foregoing objects and advantages of the invention are still further attained by providing a method of isolating a target component from a sample, comprising the steps of: contacting a solution or dispersion of the target component with a magnetically responsive microbead having a coating with a binding affinity for the target component, the contacting step being for a sufficient time to enable the target component to bind to the beads; activating a probe to induce an electromagnetic field to the dispersion and capturing the beads on the probe; transferring the probe and captured beads to a first washing liquid; and deactivating the probe to release the beads into the washing liquid to remove impurities and isolate the target component.

The foregoing objects and advantages of the invention are yet further attained by providing a method of analyzing a target component comprising the steps of: contacting a solution or dispersion of a target component with an amount of magnetically responsive microbeads having a coating with a binding affinity for the target component, aspirating the solution or dispersion through a tube having a filter device and collecting the beads on the filter device, positioning an end of the tube in an inlet of an analytical device; and eluting the target component from the beads directly into the analytical device and analyzing the target component. The contacting step is for sufficient time for the target component to bind to the beads.

The foregoing objects and advantages of the invention are further attained by providing an apparatus for recovering an amount of magnetically responsive beads from a liquid. The apparatus comprises a vessel for Containing a liquid having an amount of magnetically responsive beads; and a probe mounted for reciprocating movement into and out of the vessel. The probe is capable of selectively producing an electromagnetic field. The probe has a top end and a bottom end land a collar coupled to the top end.

The foregoing objects and advantages of the invention are still further attained by providing an apparatus for separating a target compound from a solution or dispersion. The apparatus comprises a first vessel for containing a first electrically conductive liquid; a second vessel for containing a second electrically conductive liquid, the second liquid containing the target compound; a first electrode positioned in the first vessel for making electrical contact with the first liquid; a second electrode positioned in the second vessel for making electrical contact with the second liquid; a porous member coupled to the second vessel for separating the first liquid from the second liquid while allowing an electric current to pass between the electrodes; an amount of magnetically responsive beads having a coating of material with an affinity for the target compound; the beads being positioned on the porous member, and an electrical power source for producing an electric current between the electrodes to cause the target compound to migrate toward the beads to bind with the coating material.

The foregoing objects and advantages of the invention are further attained by providing an apparatus for separating a target compound from a solution or dispersion. The apparatus comprises a hollow tube having a first open end and second open end, and has an axial passage between the first end and the second end; a porous filter member disposed in the axial passage; an aspirating device coupled to the second end of the tube; and a magnet for producing an electromagnetic field in the axial passage for capturing magnetically responsive beads.

The foregoing objects and advantages of the invention are further attained by providing an apparatus for transferring magnetically responsive beads. The apparatus comprises a first vessel having a closed bottom end and an open top end, the first vessel being dimensioned for containing a liquid containing an amount of magnetically responsive beads; a second vessel having a closed bottom end and an open top end, the open top end of the second vessel being in communication with the open top end of the first vessel; and a first magnet for capturing the beads from the first vessel and transferring the beads to the second vessel.

BRIEF DESCRIPTION OF THE DRAWINGS

The following is a brief description of the invention, in which:

FIGS. 9–14 are, cross-sectional views showing the sequential steps of the separation apparatus of the embodiment of FIGS. 7 and 8;

DETAILED DESCRIPTION OF THE INVENTION

Figure 1:
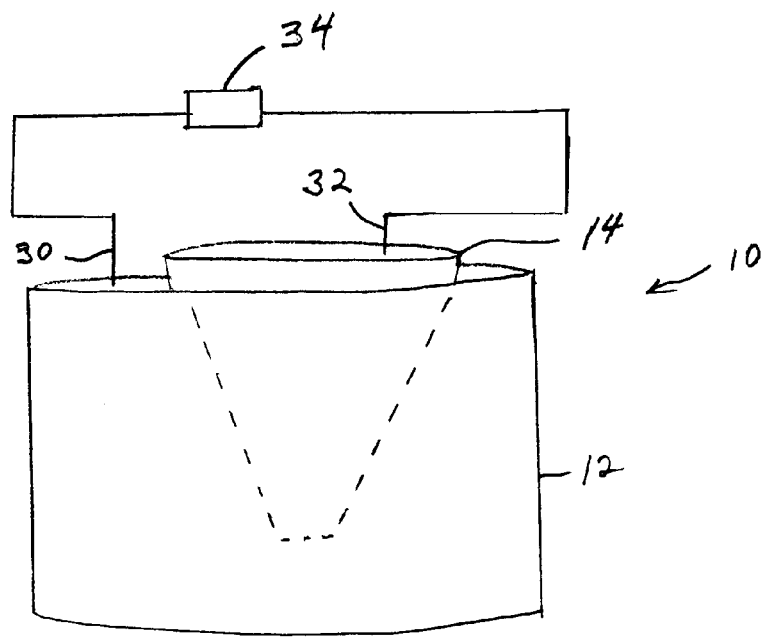
FIG. 1 is a perspective view of the separation apparatus in a first embodiment of the: invention.

The term "isolated" when referring to a protein, means a chemical composition that is essentially free of other cellular components, particularly other proteins. The term "purified" refers to a state in which the relative concentration of a protein is significantly higher than a composition in which the protein is not purified. Purity and homogeneity are typically determined using analytical techniques such as polyacrylamide gel electrophoresis or high performance liquid chromatography. Generally, a purified or isolated protein will comprise more than 80% of all macromolecular species present in the preparation. Preferably, the protein is purified to greater than 90% of all macromolecular species present. More preferably, the protein is purified to greater than 95% and most preferably, the protein is purified to essential homogeneity, or wherein other macromolecular species are not significantly detected by conventional techniques.

The term "protein" is intended to also encompass natural and artificially derivitized variant molecules such as glycoproteins, lipoproteins and labeled proteins as well as lower molecular weight peptides. Polypeptide subunits of a holoprotein are considered proteins as well. "Peptides" generally refer to fragments of proteins regardless of size in the present application.

"Small molecules," are low molecular weight preferably organic molecules that are recognizable by receptors. Typically, small molecules are specific binding compounds for proteins.

The terms "binding component", "ligand" or "receptor" may be any of a large number of different molecules, and the terms can be used interchangeably.

The term "ligands" generally refers to chemical components in a sample that will specifically bind to receptors. A ligand is typically a protein or peptide but may include small molecules, particularly those acting as a hapten. For example, when detecting proteins in a sample by immunoassay, the detected proteins are the ligands.

The term "receptors" refers to chemical components in a reagent, which have an affinity for and are capable of binding to ligands. A receptor is typically a protein or peptide but may include small molecules. For example, an antibody molecule frequently acts as a receptor.

The term "binding member", as used herein, refers to a member of a binding pair, i.e., two different molecules wherein one of the molecules specifically binds to the second molecule through chemical or physical means. In addition to the well-known antigen and antibody binding pair members, other binding pairs include, but are not intended to be limited to, biotin and avidin, carbohydrates and lectins, complementary nucleotide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), sugar and boronic acid, and similar molecules having an affinity that permits their association in a binding assay. Furthermore, binding pairs can include members that are analogs of the original binding member, for example an analyte-analog or a binding member made by recombinant techniques or molecular engineering. If the binding member is an immunoreactant it can be, for example, an antibody, antigen, hapten, or complex thereof, and if an "antibody" is used, it can be a monoclonal or polyclonal antibody, a recombinant protein or antibody, a chimeric antibody, a, mixture(s), single chain antibodies, phage display antibodies (including the whole phage), or fragment(s) thereof, as well as a mixture of an antibody and other binding members.

The term "bind" includes any physical or chemical attachment or close association, Which may be permanent or temporary. Generally, an interaction of ionic bonds, hydrogen bonding, hydrophobic forces, van der Waals forces etc., facilitates physical attachment between the ligand molecule of interest and the receptor. The "binding" interaction may be brief, as in the situation where binding causes a chemical reaction to occur. This is typical when the binding component is an enzyme and the analyte is a substrate for the enzyme. In addition, chemical coupling may be a permanent or reversible binding. Reactions resulting from contact between the binding component and the analyte are within the definition of binding for the purposes of the present invention. Binding is preferably specific. The, binding may be reversible, particularly under different conditions.

The term "bound it" or "associated with" refers to the tight coupling of the two components mentioned above. The nature of the binding may be chemical coupling through a linker moiety, physical binding or packaging such as in a macromolecular complex. Likewise, all of the components of a cell are "associated with" or "bound to" the cell.

An "affinity label" is a chemical moiety bound to a protein of interest that one wishes to manipulate through binding to the affinity label. Usually, affinity labels are attached to the protein via a linker group and an optional spacer group to hold the protein at a distance from a receptor for the affinity label. Typical affinity labels include all types of ligands and receptors, particularly biotin, and haptens.

The term "biological sample" includes tissues, fluids, solids (preferably suspendable), the whole organism, extracts and fractions that contain proteins. These protein samples are from cells, tissues or fluids originating from one or more plants, microorganisms or animals. In the present invention, the source is generally a mammal.

The term "bead" refers to a small particle that fits inside the collection and reaction vessels used in the present invention. The bead interacts with one or more proteins by itself or through an added moiety or coating.

The term "magnetically responsive" refers to material that is itself magnetic, may be made magnetic temporarily or is responsive to a magnetic field. These include paramagnetic, diamagnetic, ferromagnetic, supermagnetic, etc. materials. Particularly preferred are paramagnetic particles as they loose their magnetism whereas ferromagnetic particles remain magnetic even when such is not desired. The term may refer to materials with different properties such as a permanent magnet rod and small iron-containing beads. Also included in the term "magnetically responsive" are highly charged beads that are readily movable in an electric field, and thus, electrically responsive beads are included.

The term "permeable support material" is a solid material through which proteins or peptides can pass in a manner whereby a mixture of proteins or peptides can be separated. Gels, especially electrophoretic gels, are particularly preferred.

The present invention is directed to the recovery and subsequent use and identification of proteins separated on two-dimensional (2-DE) electrophoretic gels. The 2-DE separated proteins are recovered in a form that efficiently captures the protein, since the amount of protein in the gel is typically very small. Because the number of different proteins isolated in the gel is large, the present invention is designed to be compatible with automation. When needed, the present invention is compatible with processes to renature the unfolded protein molecules denatured during electrophoretic separation, particularly with respect to antibody binding to the protein for either immunoassays for detection of either the protein or the antibody, to select monoclonal, single chain, polyclonal or fragments of antibodies that bind to them or to repeatedly capture protein-specific antibodies from an antibody mixture (e.g., one produced by immunization with pooled antigens). Such uses may be performed cyclically to generate many times more antibody than the molar amount of immobilized antigen from the gel spot.

With the antibody, one may immobilize it to make an affinity chromatography column and use the antibody to purify even more antigen from gels or natural sources and continue the process to bootstrap the methods to obtain even more antibody and then even more antigen, etc. until almost any quantity of either can be obtained.

The use of magnetically responsive beads coated with protein binding moieties provide means for easily transporting the immobilized proteins so as to expose them to a succession of different liquid reagents, including antibodies and other protein samples, and in a manner consistent with high throughput robotic sample handling.

Because the quantity of protein in each gel spot is small, the protein can easily be lost by adsorption to a surface. This is particularly a problem with plastic surfaces. Throughout the apparatus of the invention, the surfaces are preferably coated with a "blocking agent" to passivize the surface to prevent the protein from being lost. Suitable blocking agents include collagen, gelatin (particularly cold water fish skin gelatin), skim milk, serum proteins, and a large number of compounds having a hydrophobic moiety and a hydrophilic moiety that are not reactive with proteins.

The choices of how to isolate a protein separated on a two-dimensional gel and flake it available for further manipulation are limited. One method in the art is binding the protein to a membrane, which can be in the form of a large sheet with many proteins immobilized on the sheet in the same spatial relationship as existed in the 2-DE separation (i.e., a Western blot). Alternatively, the blot can be made or cut into small pieces, or pieces mounted in arrays (e.g., in the bottoms of 96 well plates). Immobilization on a membrane (as in Western blotting) is effective in recovering the proteins for subsequent detection (e.g., by colloidal gold stains), but the membrane zones to which individual proteins are bound are difficult to separate for individual handling in subsequent steps. Complete recovery of the proteins from a membrane is difficult, which makes the recovery not quantitative. If the blotting is done on individual spots (e.g., in 96-well filter bottom plates where the filter is a protein-binding membrane such as nitrocellulose or PVDF), the filter area tends to be much larger than the spot (at least with current plates) leading to problems with non-specific binding on the rest of the filter. The application of antibody mixtures and wash solutions to the immobilized spot proteins involves repeated flows over many well filters.

An alternative method is electroelution from an isolated excised gel region (ideally containing one protein) in an apparatus designed to "catch" the protein by placing an ion-permeable but protein impermeable membrane in its path in the direction of migration toward the anode. Ideally, the protein can be collected in a small amount of liquid near the membrane surface and later used for structural characterization or immobilized on a surface for further work. To reduce the volume, immobilization on a surface such as a 96 well plate well is preferred. The protein is fixed in terms of its density and in terms of its relationship with other immobilized proteins.

A common problem with the elution methods is that the protein is not easily recovered in a small volume, at high efficiency with little loss (to obtain quantitative results) and in a form easy to further manipulate by robotic methods. Recovering all the protein in the gel piece in a form that faclitates further manipulation allows for quantitative measurements and more efficient utilization of the separated proteins for several purposes. Because the amount of protein in a two-dimensional gel spot is so small, a high level of recovery of protein is needed for many purposes. The present invention avoids these difficulties by using beads coated with a material to adhere to the proteins or affinity moieties attached thereto. Small magnetically responsive beads are particularly preferred as they can be easily manipulated, washed, placed in small volumes of reagent and have the proteins recovered in small volumes.

The protein can be immobilized on the beads by covalent chemical bonds, strong, specific non-covalent ligand-receptor bonds or weaker non-covalent bonds. Ligand-receptor bonds include biotin-streptavidin/avidin or antibody-antigen interactions. While biotin-streptavidin is non-covalent, it has a very high affinity (dissociation constant of about $10^{15}$), and is preserved under a range of room temperature solution conditions that can be used to dissociate antibodies from antigens (e.g., pH 2, 4 M guanidine, 2M ammonium thiocyanate, or 1% SDS). The streptavidin itself is very stable, and is unlikely to be released from the beads during the manipulations required for magnetically responsive beads. Weaker non-covalent bonds include hydrogen bonds, hydrophobic attractions, etc. such as those between PVDF and a protein adsorbed on a membrane of these materials.

Other chemical affinity moieties may be used such as hapten or epitope derivitized protein and an anti-hapten or anti-epitope antibody bound to the beads. After affinity binding, the attachment may be made permanent by chemical crosslinking to form a covalent bond. Organic chemical moieties may also be used as binding members where the protein and bead surface are derivitized with such binding members as lectins with sugars or polysaccharides, Protein A or G and antibody Fc, hormones and hormone receptors, T-cell receptors and antigens, coenzymes/cofactors and enzymes, phenylboronic acid with salicylhydroxamic acid and other pairs of chemical moieties reactive to each other but not proteins in general.

Either a covalent or a very strong non-covalent bond is preferred to allow repeated use of the immobilized protein. The biotin-labeling approach has the advantage that the protein can be separated from the beads by a long extender arm (part of the biotinylation reagent), and this should assist in renaturing the protein. Most direct protein:bead covalent immobilization chemistries and non-specific adsorption will bind the protein very close to the bead and are likely to bind it at more than one site, inhibiting possible refolding of the protein. On the other hand, the use of an affinity label such as biotin requires use of beads coated with the proteins avidin, streptavidin, or analogs, with the attendant possibility that antibodies or other molecules interacting with these proteins could generate unwanted "non-specific" binding. Antibody/antigen binding can be either direct and close or through ah affinity label and sufficiently removed to permit renaturation of the protein.

In a two-dimensional gel, a typical protein spot detectable by Coomassie Blue staining contains perhaps 100 ng protein, which equals about 2 pmol ($2 \times 10^{-12}$ mol) if the protein has a MW of 50 kd. Assuming the area of a protein is roughly 5 nm×5 nm ($25 \times 10^{-18} m^2$) when bound on a surface, then 2 pmol will take up 0.3 cm$^2$ in total area, when closely arranged on the surface, and 1 $\mu$g will require 3 cm$^2$. Hence, the amount of protein in a 2-D gel spot (generally ~100 ng) can generally be bound quantitatively to the inside of a 96-well plate well, or to a small volume of beads, if the surface can accommodate them at high density. In the case of avidin-coated Poros® support beads (BA Poros), 12.5 $\mu$-mol of biotin can be bound per 100 $\mu$l Poros® support beads. For a 60 kd biotinylated protein, 1 $\mu$g protein should be taken up by 0.13 $\mu$l of the Poros® support beads. Because the beads are porous with great internal surface area, a very small volume of beads may be used. The binding capacity of Dynal streptavidin beads is about 5–10 $\mu$g biotin labeled protein per mg of beads.

Hence, an object of the present invention is to provide a method for the recovery of a large fraction of the gel spot protein by adsorption onto magnetic beads. When the protein has been taken from a two-dimensional gel run under denaturing conditions, the protein is denatured. Once the protein is adsorbed to the beads, directly or via an affinity ligand, the composition is one of a denatured protein bound to the bead. The beads can be further manipulated by use of appropriate magnetic fields to perform processes such as digestion with protease, exposure to antibody mixtures in order to select those antibodies that specifically bind to the protein, and exposure to other proteins that may or lay not be found to bind to the original protein.

The magnetically responsive beads are preferably small beads of polymers, glass or other inert material with particles of magnetically responsive material impregnated therein. Soft iron particles are particularly preferred in which the magnetic properties are based on superparamagnetism of the iron, such that the beads bind to a permanent or electromagnet, but not to one another in the absence of an external magnetic field. Preferred examples include plastic magnetic beads produced by Dynal (Norway), paramagnetic particles and superparamagnetic beads produced by Bangs Labs, Advanced Magnetics, Fluorescent and brightly colored magnetically responsive particles, Spherotech (Libertyville, Ill.) and Bangs Labs, porous or solid surface beads, ferromagnetic nickel beads (Clemente Associates), polysaccharide (dextran) coated magnetic beads, silica and controlled pore glass magnetic beads (U.S. Pat. No. 6,027, 9456). The beads are added as a small volume of slurry to the elution chamber such as a plugged, buffer-filled pipette tip and moved downwards to form a dense zone atop the plug by means of gravity or a magnet placed beneath the sharp (bottom) end of the pipette tip. The beads tested do not move from this position during electroelution.

The beads themselves are preferably between about 10 nm and about 1 mm in diameter and have a specific gravity greater than about 0.5 and less than about 8. More preferred, are beads in the range from 0.1 to 5 $\mu$m as they will remain suspended for a few minutes. The beads can have an inert polymer coating on the magnetically responsive particle or a plurality of such particles may be embedded in an inert polymer. When peptides are to be bound to the bead (as in the embodiments aiming to recover peptides from a protein spot digest) the polymer is preferably derivitized to include a hydrophobic coating or copolymerized with a hydrophobic monomer such as one having a $C_{18}$ hydrocarbon side chain. The magnetically responsive portion of the bead can be in the form of particles, wires, strips, electroplated, deposited or lithographically formed sections which contain iron but may also include nickel, cobalt, alloys of the same, alloys of magnetic rare earth elements or other paramagnetic materials.

In alternative embodiments, the "magnetically responsive" beads are highly charged such that they are movable in an electrical current. In this embodiment, a pair of electrodes is inserted into the vessel and a high voltage current is applied to attract the beads to one electrode that is then removed from the vessel with beads attached. The beads are released by ceasing the electric current.

The magnetically responsive beads are generally not used in their native form but are coated with specific materials that have the desired binding properties. In one embodiment, the magnetically responsive beads are made from polymeric materials with magnetically responsive particles embedded therein. For the purposes of this application, this outer layer is considered a "coating".

The coating is preferably a polymeric material having pendant moieties that bind to essentially all of the proteins and/or peptides of interest. The pendant moieties are generally hydrophobic to make the coating hydrophobic. The pendant group is generally an acyclic hydrocarbon having at least 4 carbon atoms. In a preferred embodiment, the pendant group is an alkyl group of from 4–30 carbon atoms. In other embodiments, the pendant group is a $C_8$ to $C_{25}$ alkyl, and preferably a $C_{18}$ alkyl. Cyclic, aromatic, heterocyclic and branched hydrocarbons with or without alkene moieties can also be used. The pendant groups can contain oxygen, nitrogen, sulfur, halogen, and phosphorous containing groups. The critical feature is that the coating adsorb essentially all proteins or peptides from an aqueous solution and bind them sufficiently that they are not washed off.

The coated beads can be synthesized by chemically attaching the coating onto a magnetically responsive bead or by modifying commercial C18 particles so that they become magnetically responsive. The latter may be done by using commercial octadecylsilyl silica beads, microBondapak® C18 packing, or Sep-Pak® C18 cartridge packing and impregnating them with iron by photolithography, adherence or covalent attachment to iron containing particles. As used herein "C18" coated beads refers to beads having a coating where the coating is a polymeric material having $C_{18}$ alkyl pendant groups.

Polystyrene has been used in the prior art to form beads and these adsorb some but do not adsorb all peptides or proteins well. Elution from polystyrene beads is also erratic. This appears to be particularly true for charged peptides. By contrast, the present applicants have better success with C18 coated magnetically responsive beads.

Once the bead has adsorbed the desired protein(s) or peptides, one may add a blocking agent to prevent the beads from adsorbing any further proteins or peptides. Since proteins are ubiquitous in the environment and found in many solutions that may be used to contact the protein or peptide bound beads, undesired binding is important to be kept to a minimum. The exception to this general procedure is when one wishes to later elute the protein or peptide for a purpose where pure protein or peptide is required such as in MS analysis.

The nature of the binding between protein or peptide and the coating is such that the binding reaction can be reversible under different conditions than that used to dissociate the protein or peptide binding to other materials to be added later. For example, protein antigen bound to C18 coated magnetically responsive beads are elutable with about 50% acetonitrile in water but not pH 2.5 buffer alone whereas antibody bound to the antigen is elutable by the acidic buffer but not acetonitrile. By using different binding reactions between beads and proteins/peptides than between the bound proteins/peptides and added binding member, each may be selectively elutable at will.

For certain proteins, adherence to a hydrophobic coating is desirable as the hydrophilic portions of the molecule, which usually represent the antibody, binding epitopes, are freely available. However, for other proteins, adherence to a hydrophobic coating may result in denaturation. Where denaturation is such that the protein may no longer act as a binding member, the magnetic beads should not be coated with a hydrophobic material. Instead, the beads should be coated with affinity binding reagents for a naturally occurring, chemically added epitope, or binding moiety on the protein. For example, the protein can be biotinylated and contacted with avidin coated beads.

Figure 2:
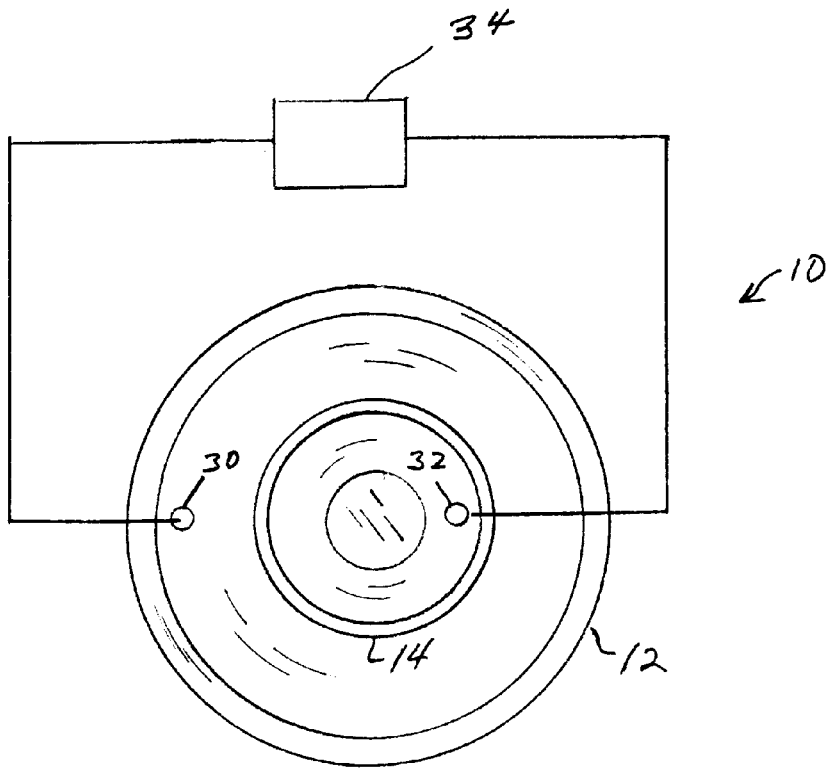
FIG. 2 is a top view of the apparatus of FIG. 1.
Figure 3:
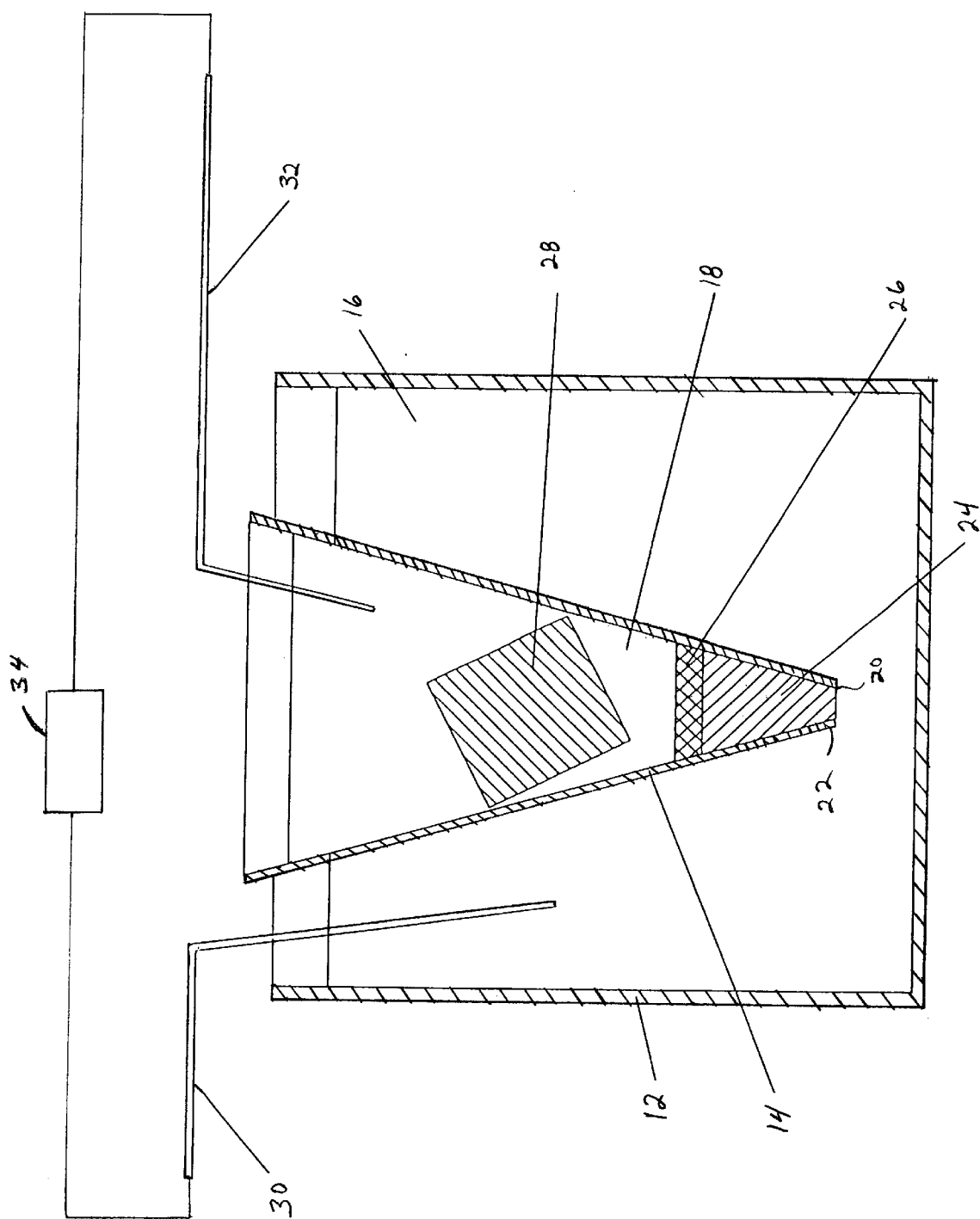
FIG. 3 is a cross-sectional side view of the separation apparatus of FIG. 1.

In a first embodiment of the present invention shown in FIGS. 1–3, an electroelution apparatus 10 includes a first vessel 12 and second vessel 14 for containing a first buffer solution 16 and a second buffer solution 18, respectively. The buffer solutions are standard buffers as known by one skilled in the art of electroelution processes. Preferably, second vessel 14 is made from an electrically insulating material. In the embodiment illustrated, second vessel 14 has a conical shape, but can have any shape. In one embodiment of the invention, the second vessel 14 is made from a disposable pipette tip and is suspended in first vessel 12. Second vessel 14 has an opening 20 at a bottom end 22 that is plugged by a piece of acrylamide gel 24 formed by polymerizing 2 μl of gel in the open end 20 of vessel 14. A screen or other porous structure, such as glass wool, may be substituted for acrylamide gel 24. The acrylamide gel plug 24 contains a buffer so that it conducts electrical current, but prevents any bulk flow of liquid between the space within first vessel 12 and second vessel 14. A layer of coated paramagnetic beads 26 lies atop the acrylamide gel plug 24. A gel spot 28 that is excised from a 2D gel slab containing a protein spot, is placed above beads 26 and is submerged in buffer solution 18. Platinum wire electrodes 30 and 32 positioned in first vessel 12 and second vessel 14, respectively, provide electrical connection for the passage of current through the gel spot 28, beads 26 and gel plug 24. Electrode 32 is typically the cathode (negative), and electrode 30 is the anode (positive) and are connected to a suitable power source 34.

Electric current is applied between the electrodes 30 and 32 for a predetermined period of time, depending upon the nature and amount of material to be moved from the gel spot 28 to the beads 26. The level of current also depends upon the nature and amount of material in the gel spot 28. For instance, a voltage of between about 10 volts and 500 volts can be applied, but ideally, about 50 volts is applied. During the application of the electric current, desired material in the gel spot 28 moves from the spot 28 toward the electrode 30. However, the desired material is captured by the beads 26 and remains attached to the beads 26 so long as the voltage between the electrodes 30 and 32 is not applied for an inappropriately long time period at tool high a voltage.

Once the electroelution is completed and the gel spot protein (optionally derivitized for example with biotin) is captured by the beads 26 (optionally derivitized for example with streptavidin), the electrode 32 and gel spot 28 are removed, and the paramagnetic beads 26 recovered onto a magnetic probe, as discussed hereinafter, for transfer to another container. Other containers include wash solution, renaturation solution, elution solution, antibody or other receptor solution, etc.

In this embodiment using the apparatus of FIGS. 1–3, the procedure is used to capture protein from a gel spot 24 onto paramagnetic beads 26. A two-dimensional electrophoretic separation is performed using a protein sample which can be biotinylated or otherwise chemically modified to provide an affinity binding agent. One preferred affinity label or hapten was formed by adding a small moiety of very low molecular weight that preserves the protein's net molecular charge and Isoelectric point. One such example is the biotinylation of the protein with the reagent NHS-iminobiotin (Pierce). Other examples of affinity binding pairs include lectins and sugars, haptens and antibodies, Protein A or G and antibody Fc, other specific binding protein pairs, phenylboronic acid with salicylhydroxamic acid and other pairs of chemical moieties reactive to each other but not proteins in general.

A two-dimensional electrophoretic gel is optionally stained and a desired protein spot identified. The portion of the gel containing the desired protein spot is cut out, physically removed or isolated from the remainder of the gel to obtain gel spot 28, such as by placing second vessel 14 over the gel spot location on the gel slab, with or without the opening of the vessel cutting into the gel slab. The gel spot 28 is placed into the second vessel 14 of FIG. 1 and an electric current is applied, causing the protein (now complexed with SDS) to migrate out of the gel spot 24, through the buffer 18 and over a bed of coated beads 26. The bed of beads 26 can be formed by sedimentation or by a magnet placed next to the vessel. When the protein is biotinylated before electrophoresis or while still in the gel, avidin or streptavidin-coated paramagnetic beads are used, and the biotinylated gel spot protein is bound via the biotin-avidin or streptavidin interaction. Other affinity labels may be attached to proteins and used in combination with a corresponding receptor for the affinity ligand. The receptor is attached to; the magnetically responsive beads. When the protein spot is biotinylated after the electrophoretic separation in the gel, biotin alone (NHS-biotin) can be used since charge modification is not required at that time. It has been found that biotin and biotinylated proteins bind to streptavidin in the presence of the SDS denaturant.

In as much as C18 coated beads non-specifically adsorb essentially all proteins and peptides, those of the present invention can be used to adsorb mixtures of proteins and can be used as an all protein purification and concentration technique in the same manner as other protein adherent materials have been used previously such as the sides of plastic tubes during immunoassays and the like. Additionally, C18 coated beads are used to adsorb proteins in conventional column chromatography and the present invention may use the C18 coated magnetic beads for the same purposes, once made paramagnetically responsive, particularly after the protein has been adsorbed onto the beads. Better adsorption due to dispersion may result compared to using a prefilled column for HPLC and the like. Magnetically responsive beads are easier to manipulate during the column filling.

In a further embodiment, the magnetically responsive beads have a coating with a reactive group capable of covalently bonding with the proteins on contact. The bound protein can be used to isolate antibodies. Alternatively, the antibody can be bound to the beads and the beads used to isolate proteins.

In another embodiment, an affinity label is attached to the protein(s) before, during or after the initial SDS electrophoresis. In this embodiment, the proteins migrating within or between gel supports are exposed to a reactive form of an affinity label, which then covalently binds to the proteins. Since these reagents for adding an affinity label are small molecules, they may be added directly to and react with proteins in solution or in the gel itself without prior separation. A part of the gel, such as an excised spot may be removed first from the entire gel prior to reacting to affinity label, if so desired.

During electrophoresis, denaturing conditions may be used. In order to use the proteins for certain additional purposes where the three dimensional configuration is critical, it is preferred to renature the proteins. To renature proteins, one may use decreasing concentrations of chaotropic agents such as urea or guanidine with or without disulfide rearranging agents, usually enzymes such as disulfide isomerases to assist in reforming appropriate disulfide linkages. Other renaturing techniques are known per se and may be used to restore native structure after denaturation during electrophoresis. These include gradient changing of temperature pH, surfactants, solvents, urea, guanidine, guanidine thiocyanate, ammonium thiocyanate, disulfide active reagents, etc. Disulfide active reagents include mercaptoethanol, dithiothreital dithioerythritol, glutathione, tributyl tin and the like and decreased concentrations of disulfide active agents are used at later stages of the renaturation. Additional components such as associated proteins, cofactors, antibodies and other receptors, matrixes, templates/polymers and microfilters may be added to aid the renaturing process. A considerable body of literature relating to renaturation of inclusion bodies and other proteins exists, including microsphere-induced refolding, such as Shimizu et al, Biotechnol. Prog. 16(2):248–53 (2000).

By slowly decreasing the temperature or concentration gradient of a denaturing agent of the same type, or a different type, from that which denatured the native protein originally, one enhances proper refolding of the protein. Once partially or completely renatured, the protein may be eluted from the bead or the bead can be used directly as an immobilized ligand. As the protein may still need further renaturing, the same renaturing process or by using a different gradient renaturing process may be needed. Different proteins will need different renaturing conditions, if any at all, and thus the process may be optimized for each protein recovered by binding to the bead.

Depending on the protein, solutions greater than 2M urea may contain mercaptoethanol (or another disulfide reducing agent), and solutions of less than about 2M urea can contain no such reducing agent but instead some oxygen (provided from the air or added) to allow disulfides to begin to reform.

Recovery of denatured proteins may present a problem if recovery is based on the protein being in its native state. Some antibody epitopes, binding to cofactors, associated proteins and substrates may be compromised until the protein is renatured. One advantage of the present invention is the recovery of proteins on beads by means of an interaction that is not specific to a native protein structure (e.g., via biotinylation or hydrophobic attraction), which is operable regardless of whether the protein was denatured or not. Likewise, the bead may provide a scaffolding from which renaturation can begin without concern for whether the denatured protein is soluble, and the immobilized protein is prevented from interacting with other protein molecules until after it is renatured. By omitting a resolubility step, at least one problem inherent to denatured proteins is avoided. Thus, the renaturation aspect of the present invention is broadly applicable to renaturing proteins regardless of source and particularly for inclusion bodies and proteins denatured during handling and purification. After each renaturation, one may test for enzymatic activity or receptor binding and comparing that to the natural form as a measure of the effects of renaturation.

In another embodiment of the electroelution system, the entire 2DE gel, which may be pretreated with trypsin or other peptide treating agent, is placed on a thin layer of coated magnetically responsive beads. More preferred is for a thin layer of coated magnetically responsive beads to be placed on top of the 2DE gel. The entire system is then electrophoresed to electroelute the proteins out of the gel into the layer where they are adsorbed. The region of beads containing each desired protein of interest is then removed from the bead/gel construct preferably by a punch, scoop or the like to remove a small region of beads. A magnetic probe may be used directly once the desired beads are magnetically separated from surrounding beads by a non-magnetic ring, mesh, magnetically pulled through the gel to the opposite side. The location of which beads to remove is determined by scanning the gel and using coordinates from the scan signal to a computer to control the bead removal apparatus. The gel may be scanned from the opposite side from the layer of beads or it may be scanned before the beads are ever added. Supporting the gel on a porous solid phase is recommended for proper registering of the locations of each spot as well as preventing deformation of the gel or shifting of the beads.

Contact between the beads and the gel may be enhanced by mechanically pressing, magnetically driving or centrifugally sedimenting the beads onto or into the gel. If the concentration of the protein in the spot is sufficiently high, driving coated beads into the gel and allowing diffusion and protein binding to occur may be sufficient for qualitative measurements. A mesh can be placed over the gel surface to prevent lateral movement of beads during electroelution and selective bead recovery. Since beads are then throughout the gel, including areas without any protein, proteins in spots are inhibited from diffusing from one to another as they will pass by a coated bead that should adsorb much of the protein. Once removed by cutting or driving them out of contact with the gel, they may be manipulated as any other protein coated beads of the present invention.

Figure 3A:
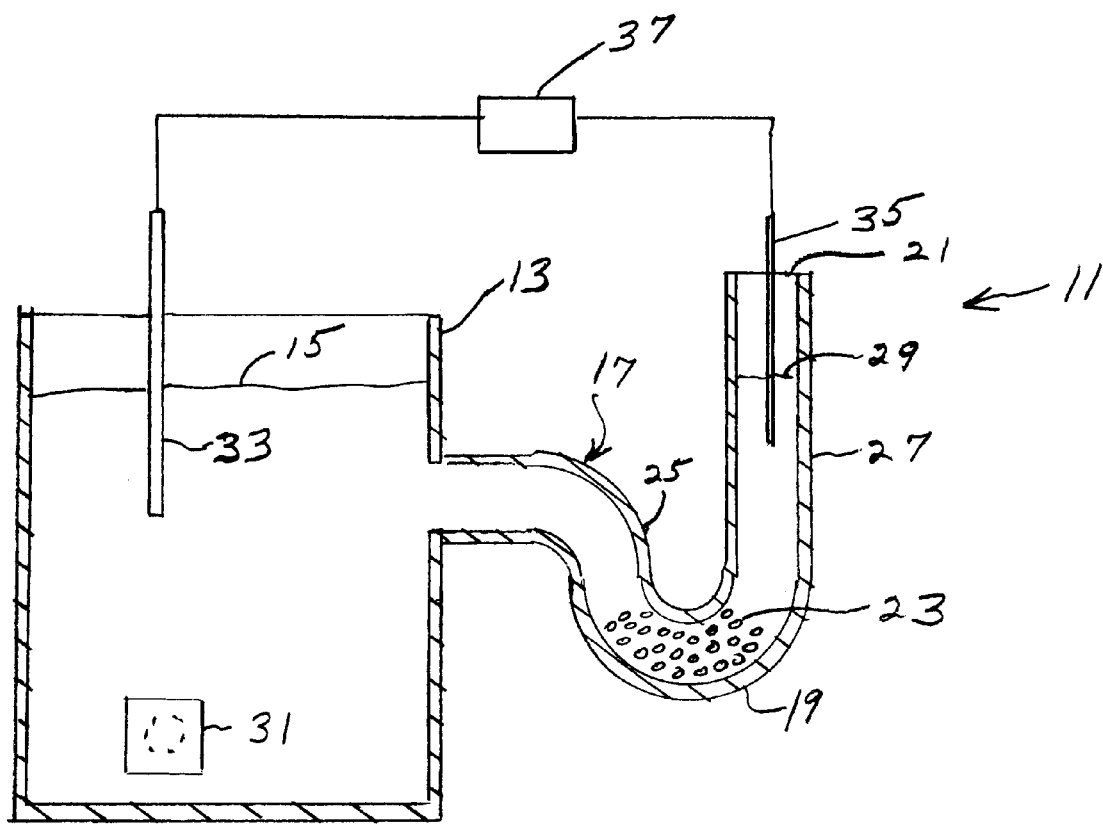
FIG. 3A is a cross-sectional side view of the electro-eluting vessel in another embodiment of the invention.

Embodiment of FIG. 3A

In another embodiment of the invention shown in FIG. 3A, an electroelution apparatus 11 includes vessel 13 for containing a first buffer solution 15. A conduit 17 extends from a sidewall of vessel 13 and includes a substantially U-shaped trap 19 and an open top end 21. A bed of magnetically responsive beads 23 having an affinity coating are placed in trap 19. U-shaped trap 19 defines a first leg 25 in communication with vessel 13 and is filled with first buffer solution 15. A second leg 27 of U-shaped trap 19 is filled with a second buffer solution 29. A gel core 31 with a protein spot and a first electrode 33 are placed in first buffer solution 15 in vessel 13. A second electrode 35 is placed in second buffer solution 29 and an electric current from a power source 37 is applied to electrodes 33 and 35 to electro-elute the proteins from gel core 31 toward second electrode 35 where the proteins or peptides are captured on beads 23. The beads 23 form a bed in U-shaped trap 19 to separate first buffer solution 15 from second buffer solution 29 without a gel plug as in the embodiment of FIGS. 1–3.

In an alternative embodiment, a protein spot is identified on a gel slab and buffer solutions are placed on both sides of the gel slab. In a preferred form of this embodiment, a first vessel having an open end is placed against the gel slab around the protein spot for containing a first buffer solution. A second vessel having an open end is placed against the opposite side of the protein spot for containing a second buffer solution An amount of magnetically responsive beads having an affinity coating is placed in one buffer solution contained in one of the vessels. Electrodes are placed in the respective buffer solutions and an electric current is applied to the electrodes to elute the protein directly from the gel slab and into solution for capture by the beads. The gel slab can be oriented vertically or horizontally and the vessels shaped appropriately to maintain the buffer solutions in contact with the gel.

In another embodiment, two adjacent vessels containing a respective buffer solution are connected by a tube or other conduit extending through the side walls of the respective vessel. A bed of magnetically responsive beads having an affinity coating are placed in the tube to separate the buffer solutions contained in the vessels. An electrode is placed in each buffer solution, and gel core containing a protein spot is placed in one of the vessels. An electric current is applied to the electrode s to elute the protein onto the beads.

Figure 6:
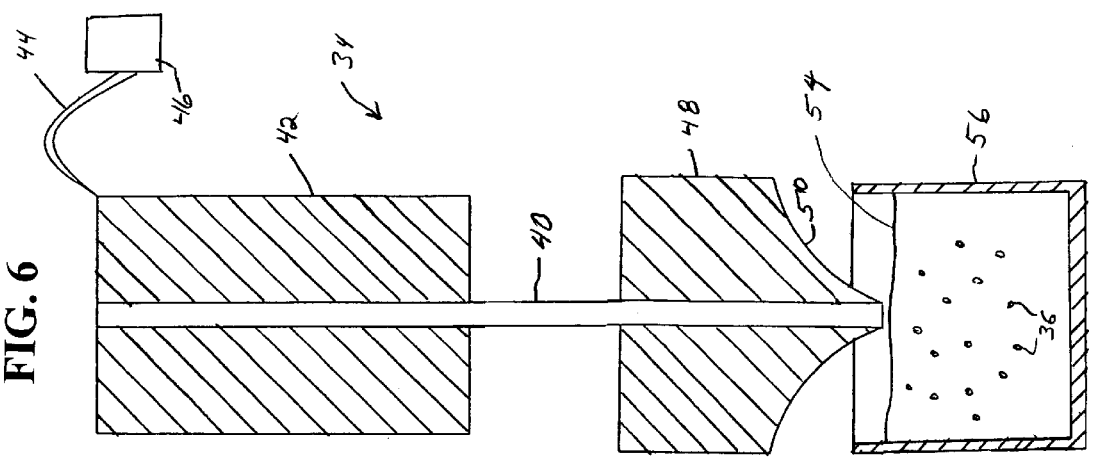
FIGS. 5 and 6 are cross-sectional side views of the probe of FIG. 4 for the separation apparatus in an embodiment of the invention showing the probe in the extended position and retracted position, respectively.
Figure 5:
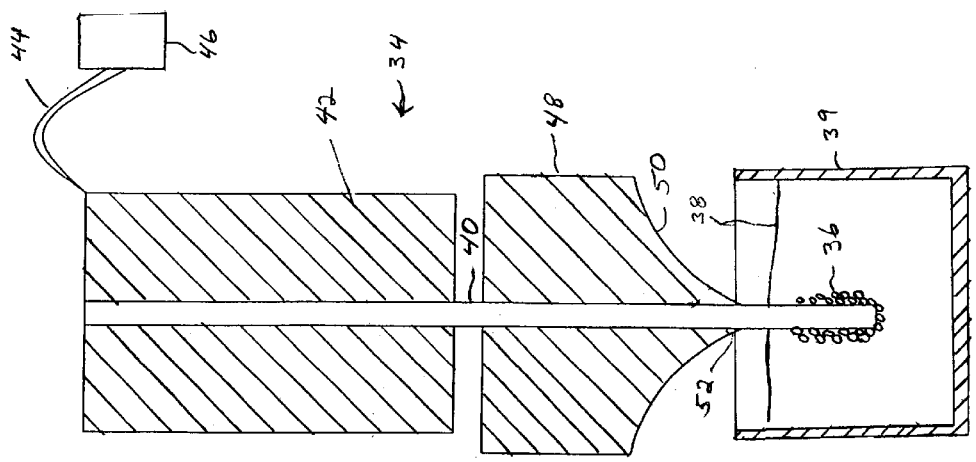
Figure 4:
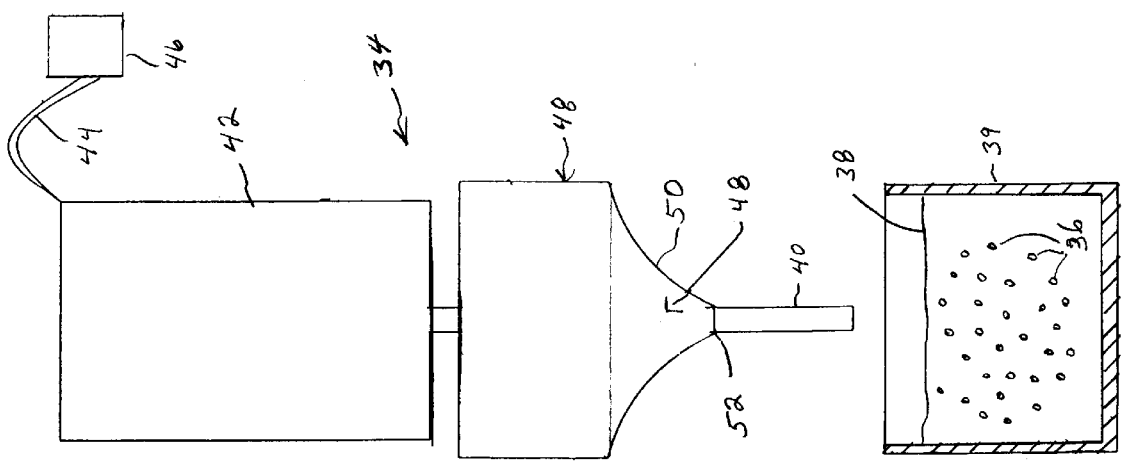
FIG. 4 is a side view of the probe in an embodiment of the invention.

Embodiment of FIGS. 4–6

This embodiment of the invention is directed to the use of a probe 34 for recovering magnetically responsive beads 36 contained in a liquid 38 in a vessel 39. Beads 36 as in the previous embodiment are coated beads having an affinity for a target component. Beads 36 are dispersed in electroeluting liquid 38 containing a target compound so that the target compound bonds to the coating on beads 36. As discussed hereinafter, probe 34 is particularly suitable for capturing beads 36 and transferring beads 36 to various washing and treatment stages.

Referring to FIG. 4, probe 34 is an electromagnet that includes core 40 of soft iron and an electrical wire coil 42. Coil 42 includes leads 44 that are connected to a suitable electrical power source 46. Power source 46 includes a suitable switching and control device for selectively applying electric current to coil 42 to activate and deactivate the magnetism of core 40. A collar 48 is coupled to core 40 and is provided with frustoconical bottom 50 converging to tip 52 on core 40. Collar 48 includes an axial passage for receiving core 40 so that collar 48 is able to slide axially on core 40.

As shown in FIG. 4, probe 34 is initially positioned above vessel 39 after beads 36 have captured the desired target component. Power source 46 is activated to magnetize core 40 and probe 34 is then inserted into vessel 39. The magnetism of core 40 captures beads 36 as shown in FIG. 5. Probe 34 is withdrawn from vessel 39 so that beads 36 can be further processed. In the embodiment illustrated in FIG. 6, beads 36 are transferred to a second liquid 54 in a vessel 56. Liquid 54 can be, for example, a washing solution to remove impurities such as excess reactants. Suitable reactants include labels or renaturing reactants as known in the art.

Beads 36 are transferred to vessel 56 by immersing probe 34 into liquid 54. Power source 46 is then deactivated to release beads 36 into liquid 54. Collar 48 is held stationary while core 40 is retracted from liquid 54. Core 40 slides through the axial passage of collar 48 so that conical tip 52 scrapes away any beads adhering to core 40. Beads 36 are: treated in liquid 54 and then recovered by inserting probe 34 in liquid 54 and actuating power source 46.

In a further embodiment, probe 34 is used to capture beads within a vessel and then the liquid is then removed from the vessel. A second treating liquid is then introduced into the vessel to wash or treat the beads that are still captured on the probe. Alternatively, an external magnet is place ed against a side wall of the vessel to capture the beads on the side wall while the liquid is replaced. The external magnet is removed to allow beads 36 to mix with the liquid.

Embodiment of FIGS. 7–15

In another embodiment of the invention shown in FIGS. 7–15, a probe 60 is mounted on a horizontal rail 62 for movement in a linear path to selected stations for transferring and processing the captured target compound. Probe 60 includes a vertical arm 64 coupled to rail 62 for horizontal and vertical movement by an actuator 66. Actuator 66 can be a pneumatic cylinder arrangement or a gear drive. Actuator 66 is coupled to a control device 68 such as a microprocessor to selectively move arm 64.

Probe 60 includes a hollow sleeve 70 having a closed bottom end 72 and an open top end 74. Typically, sleeve 70 has a generally cylindrical shape and is made of glass, plastic or other non-magnetic material. A collar 76 having an axial passage is coupled to top end 74 of sleeve 70 so that sleeve 70 extends through the axial passage. As in the previous embodiment, collar 76 has a frustoconical bottom face 78 converging to a tip 80. Typically, collar 76 is fixed to sleeve 70 and is spaced from bottom end 72 a distance to provide a working length of sleeve 70 below collar 76.

Figure 8:
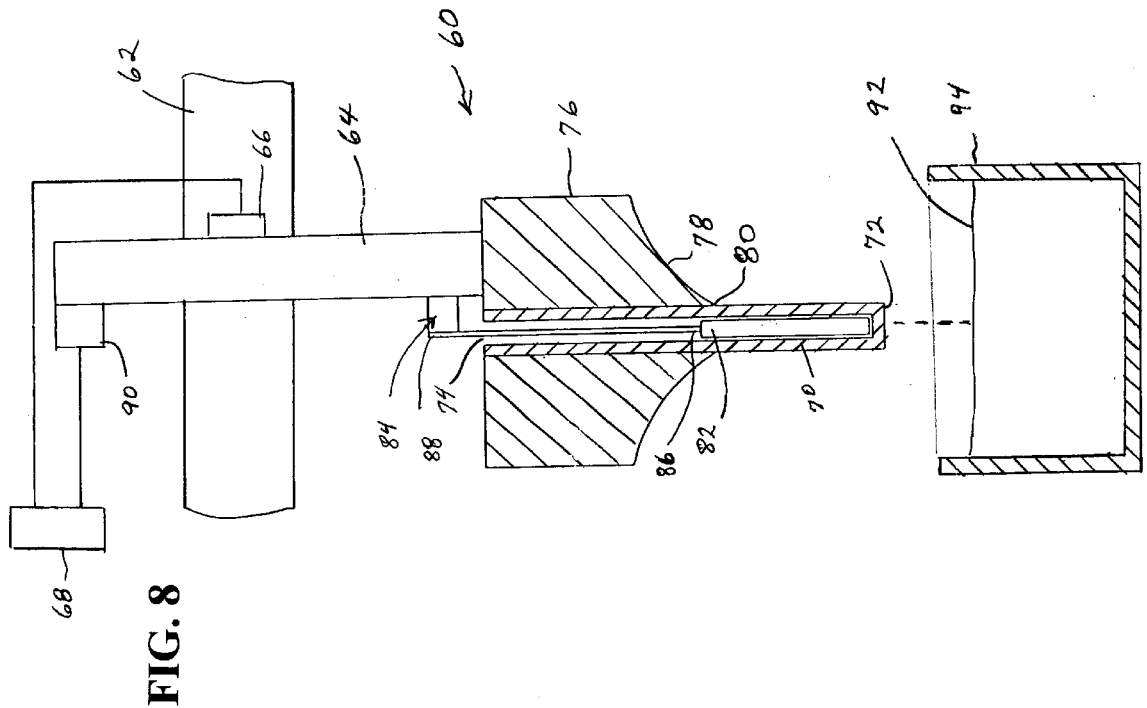
FIG. 8 is a cross-sectional side view of the probe.
Figure 7:
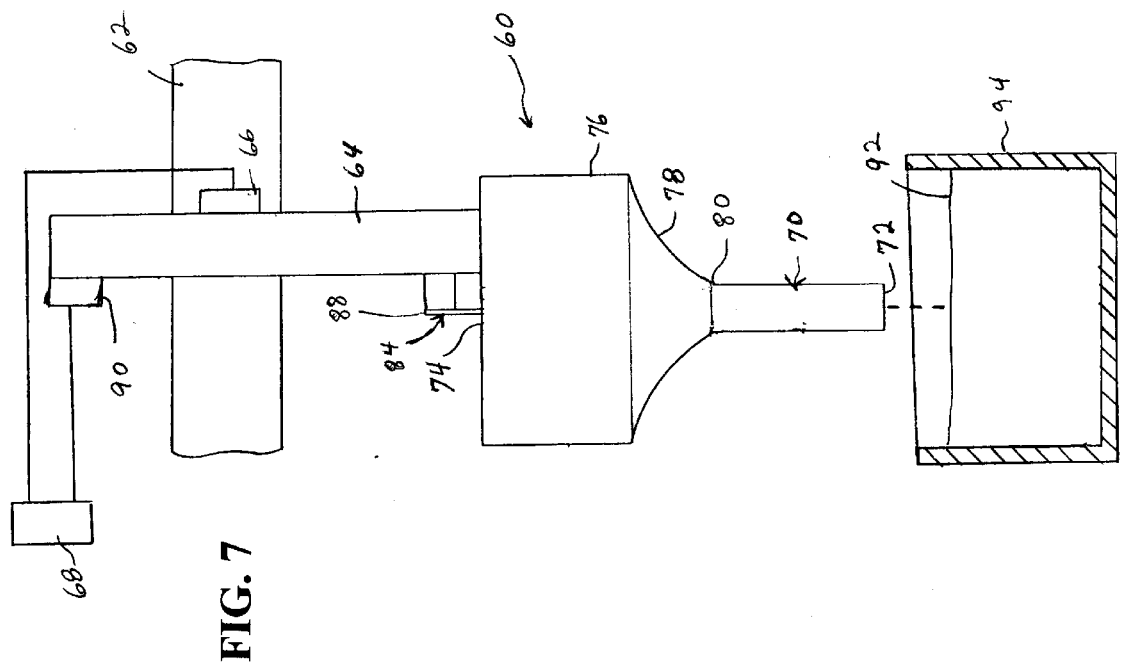
FIG. 7 is a side view of the probe for the separation apparatus in another embodiment of the invention showing the magnet in the extended and retracted position.
Figure 15:
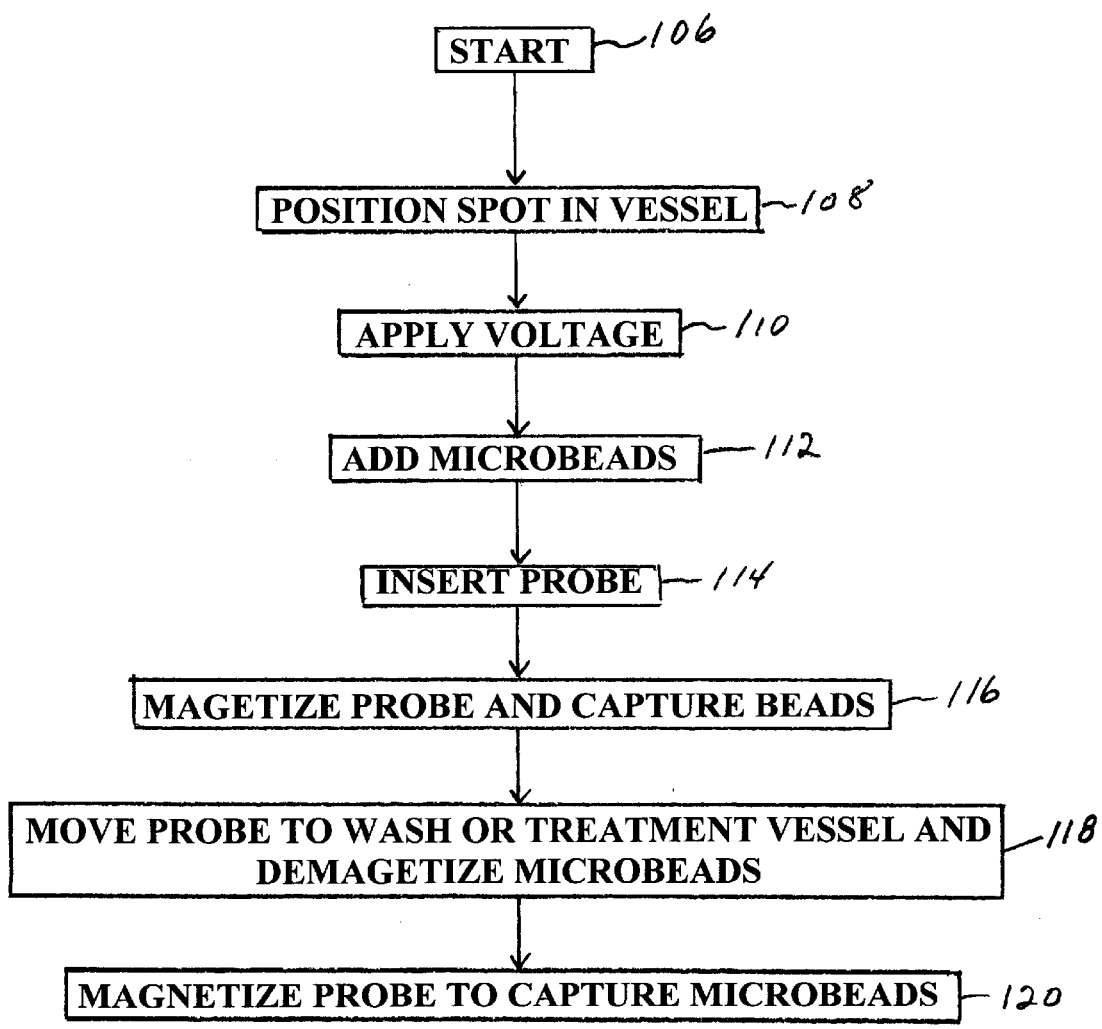
FIG. 15 is a flow chart of the process steps for capturing and releasing the beads.

Referring to FIG. 8, a permanent magnet 82 is mounted within sleeve 70 for sliding movement therein. A reciprocating arm 84 has a lower end 86 coupled to magnet 82 and an upper end 88 coupled to arm 64. Arm 64 includes an actuator 90 that is coupled to arm 84 to reciprocate magnet 82 within sleeve 70. Actuator 90 can be, for example, a pneumatic cylinder with a suitable return spring. Actuator 90 is also connected to control device 68 to selectively actuate actuator 90. Actuator 90 controls the movement of arm 64 to raise and lower sleeve 70 into and out of a liquid 92 within a vessel 94. Actuator 90 also controls the reciprocating movement of magnet 82 between an extended, down position and a retracted, raised position. When magnet 82 is in the lower position, magnet 82 is able to capture magnetic beads against the outer surface of sleeve 70. As magnet 82 is raised, the beads follow the magnet 82 until the beads reach the conical tip 80 where the beads fall free from sleeve 70.

Probe 60 is preferably used with an automated robotic assembly for processing a large number of samples sequentially. Probe 60 in one method of the invention captures magnetic beads having a target component captured on the surface thereof and transfers the beads between various vessels. Referring to FIG. 9, a vessel 96 contains a liquid 98 and magnetically responsive beads 100 dispersed therein. Vessel 96 can be a single well of a multiwell plate as known in the art. Probe 60 is lowered into liquid 98 and magnet 82 is moved to the lower position with magnet 82 adjacent closed bottom end 72 of sleeve 70 as shown in FIG. 10. Positioning magnet 82 in the lowered position of FIG. 10 attracts beads 100 and causes beads 100 to adhere to the side wall of sleeve 70. Probe 60 is then raised to the position shown in FIG. 11 to separate beads 100 from liquid 98.

Referring to FIG. 12, probe 60 is then moved to a position above a second vessel 1102 containing a second liquid 104, such as a washing solution, renaturing liquid or labeling reactant. Probe 60 with the beads 100 still captured on the surface of sleeve 70 is lowered into liquid 104. Magnet 82 is then raised to the retracted position toward top end 74 of sleeve 70 to remove the magnetic field from sleeve 70, thereby releasing beads 100 as shown in FIG. 13. As magnet 82 is raised, beads 100 tend to be pulled upward along the side wall of sleeve 70 until beads 100 reach conical tip 80 where beads 100 are prevented from following magnet 82 and fall away from sleeve 70 and are dispersed in liquid 102. Probe 60 is then raised and removed from liquid 102 to the position of FIG. 14. It will be appreciated that the capturing and transferring steps can be repeated any number of times to disperse the beads and then recapture the bead by lowering the magnet 82 into the sleeve 70.

Probe 60 is particularly suitable for use in an alternative automated method of washing beads having an affinity coating and a target component attached to the coating. An integrated method basically comprises starting the method as indicated in block 106 of FIG. 15. A gel spot containing a target component such as a protein is placed in an electroelution vessel indicated by block 108 and an electric current is applied indicated by block 110 to elute the target component into solution. An amount of microbeads having an affinity coating is added to a different type of electroelution vessel which lacks a bead layer as indicated by block 112 to capture the target component on the surf ace of the microbeads. A magnetic probe, such as that illustrated in FIGS. 9–14, is inserted into the liquid of the electroelution vessel as indicated by block 114. The probe is magnetized as indicated by block 116 to capture the microbeads. The probe is then transferred to a wash or other treatment vessel and demagnetized to release the microbeads in the wash or other treatment liquid indicated by block 120 to capture the microbeads.

In the embodiment where the protein or peptides carry an affinity label, or a reactive moiety, immobilization on the magnetically responsive beads is through a reversible interaction with a receptor on the beads or through the reactive group on the beads, which is subsequently cleavable to release the peptides from the bead.

In the situation where a protein spot excised from a gel (e.g., a 2DE gel) and digested in situ into peptides (e.g., by trypsin, lys-C, glu-C, etc.) is to be identified, beads coated with a peptide binding surface (e.g., C18) are added to the extract containing the peptides eluted from the gel piece. Because of the highly hydrophobic nature of the beads surfaces, the peptides are physically adsorbed thereon. This adsorption process may be accelerated by sonication of the gel or liquid with the beads in it.

Figure 16:
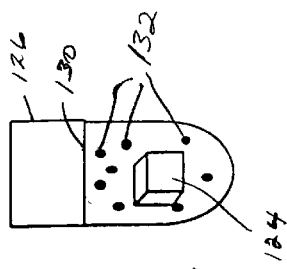
FIGS. 16A–16O are cross-sectional views showing the sequential steps for the separation and preparation of peptides for mass spectrometry in another embodiment of the invention.

Embodiment of FIGS. 16A–16O

FIGS. 16A–16O demonstrate a method in a further embodiment for the digestion of proteins into peptides for MALDI (matrix assisted laser desorption ionization) or ES electrospray mass spectrometry. A piece of excised gel with a protein spot 124 is placed in a vessel 126 containing a destaining solution 128 to remove the protein detection dye as shown in FIG. 16A to yield the destained gel spot of FIG. 16B.

The gel spot 124 is dried as shown in FIG. 16C to increase absorptive uptake followed by the addition of a digesting medium 129 as shown in FIG. 16D to cleave the proteins into peptides and rehydrate gel spot 124 Was shown in FIG. 16E. Suitable protein cleaving reagents include cyanogen bromide, pH extremes or proteolytic enzymes such as trypsin. After cleavage, an eluting liquid medium 130 is added lo vessel 126 as shown in FIG. 16F followed by the addition of magnetically responsive beads 132 to capture the peptides passively eluted from the gel spot 124 as shown in FIG. 16G.

A magnetizable probe 134, shown as a pin and electric coil, is inserted into liquid 130 to capture microbeads 132 as shown in FIG. 16H. Probe 134 with the captured beads 132 is removed from vessel 126 and inserted into vessel 136 containing a washing liquid 138 as shown in FIGS. 16I and 16J. Probe 134 is demagnetized to release beads 132 as shown in FIG. 16K where beads 132 are dispersed in liquid 138 to remove impurities from beads 132. Probe 134 is remagnetized as shown in FIG. 16L to capture the beads 132. Probe 134 is removed from vessel 136 and placed over MALDI plate 140. An eluting liquid 142, such as a 40% aqueous acetonitrile containing MALDI matrix, is directed over probe 134 to drip down probe 134 and beads 132 to elute the peptides from beads 132 onto a MALDI plate 140 as shown in FIGS. 16M and 16N. The eluted peptides are dried to form crystals 144 on plate 140 as shown in FIG. 16O.

In another embodiment, the spot is electroeluted from the gel, followed by adsorption onto the beads where it is subsequently digested into peptides. If the cleaving reagent is trypsin or other protein based reagent, it is helpful to add a blocking agent to the beads after adsorbing the protein to prevent the cleaving reagent from non-specifically adsorbing and becoming unavailable for cleavage. This embodiment has an advantage of being free of gel materials and other reagents that may interfere with the cleavage or use of the peptides at some point in another process of the present invention.

After adsorption is essentially complete, a magnetic (or reversibly magnetizable) probe is inserted into the cleavage liquid and the beads are drawn to it, where they remain as the probe is withdraw. The probe Ray now be inserted into a volume of wash liquid to remove contaminating solutes from the beads and probe. The beads may be released from the probe to be more freely washed in this liquid by temporarily de-magnetizing the probe. Alternatively, or in combination, wash solution may be dripped down the probe slowly to flow over the beads attached to the probe and thereby wash them. After washing, the probe is re-magnetized if necessary and removed from the wash liquid.

Finally the probe is brought into proximity to a MALDI MS target plate, where the beads are deposited by demagnetizing the probe. Alternatively, a droplet of eluent, such as 50% acetonitrile (ACN) flows down the probe, eluting peptides from the beads as it flows, and then deposited on the MALDI target plate. The eluent may contain other components of a matrix used for MALDI or the matrix may be separately added to the target plate before or after peptides are added.

Alternatively, the peptides may be eluted into a vessel containing a small volume of an elution solution (e.g., 50% acetonitrile in water), or else the elution solution can be dripped down the probe over the beads and recovered in a vessel. This embodiment is particularly appropriate when the peptides are to be characterized by electrospray MS.

Many other means for the magnetic control of particles are known such as U.S. Pat. No. 4,910,148 for manipulation of paramagnetic beads. Other separation techniques by magnetically controlling magnetically responsive beads may be used instead of the probes depicted in the figures.

Embodiment of FIGS. 17–22

Figure 17:
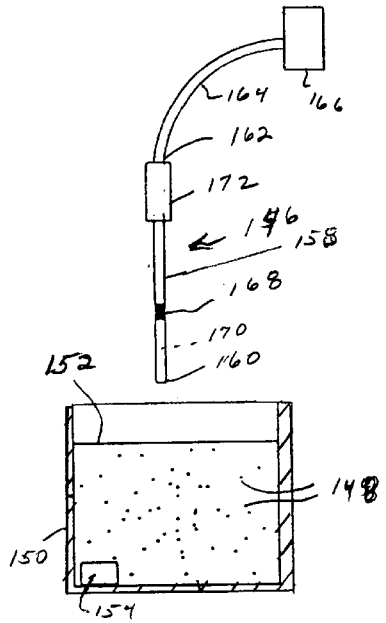
FIGS. 17–22 are cross-sectional views showing the sequential steps of the separation apparatus in a fourth embodiment of the invention.

A further method for recovering magnetic beads is depicted in FIGS. 17–22. In FIG. 17, magnetically responsive coated beads 148 are dispersed in a vessel 150 containing a protein or peptide solution 152, such as that extracted from a gel spot 154. After beads 148 adsorb the protein or peptides, beads 148 are captured by a probe 146.

As shown in FIG. 17, probe 146 includes a hollow tube 158 having an open bottom, end 160 and an open top end 162 coupled to an aspirating tube 164. Aspirating tube 164 is coupled to a control device 166 for aspirating fluid through tube 164 and for feeding a fluid through tube 164. A filter member 168 is positioned in the axial passage 170 of tube 158 and is spaced from bottom end 160. In a preferred embodiment, filter member 168 is a porous ceramic frit member having a pore size sufficiently small to collect microbeads 148. A magnet 172 having an axial passage is coupled to tube 158 such that tube 158 extends through the axial passage of magnet 172. Magnet 172 is able to slide axially along the length of tube 158. In one embodiment, magnet 172 frictionally engages the outer surface of tube 158.

Figure 18:
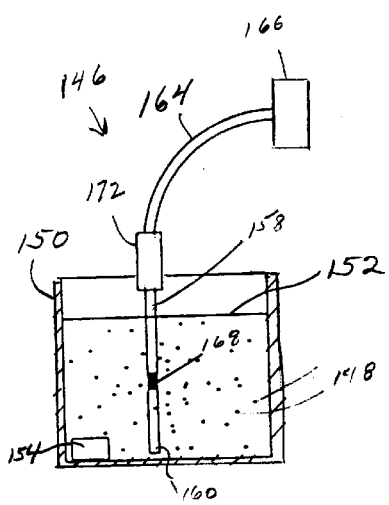
Figure 19:
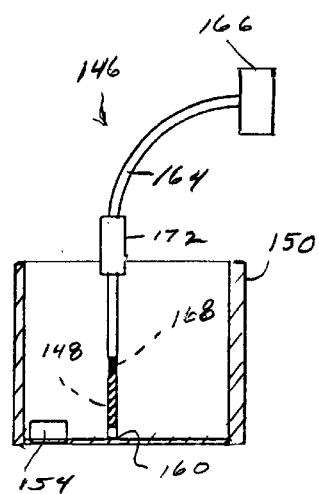
Figure 20:
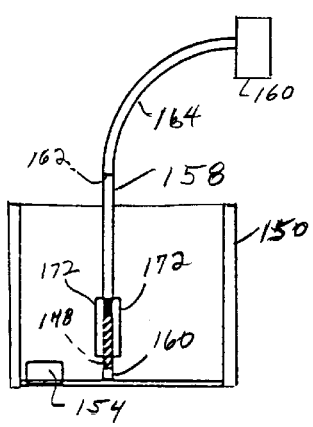
Figure 21:
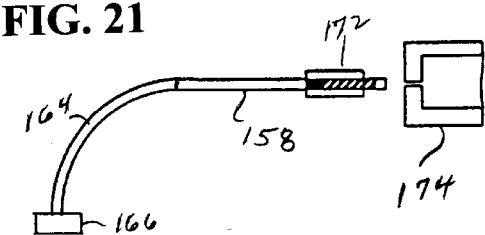

As shown in FIGS. 18 and 19, the solution 152 is withdrawn by aspiration by pumping the fluid out through tube 164 where beads 148 are retained by filter member 168 in tube 158 to form a bed of coated beads 148 shown in FIG. 19. FIG. 20 depicts the magnet 172 sliding into place to hold the magnetically responsive coated beads 148 inside the tube 158. Alternatively, magnet 172 can be positioned over tube 164 before liquid 152 is aspirated. Once the magnetically responsive coated beads 148 are immobilized in tube 158, probe 146 is removed and inserted into an analytical device 174, such as a mass spectrometer as shown in FIG. 21 or other manipulation stage such as a washing container.

Figure 22:
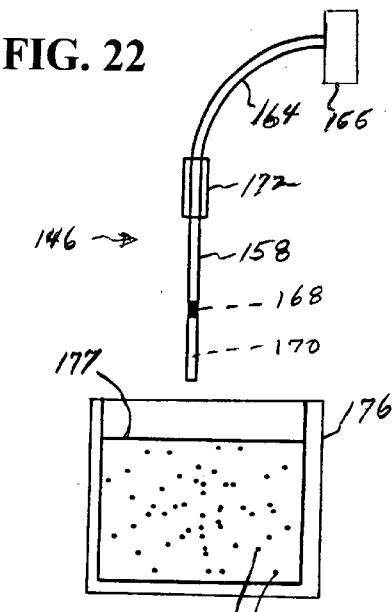

Extraction of the proteins or peptides is performed by pumping an amount of elution solution through the tube 158 and through the bed of coated beads 148 captured in tube 158 to elute the protein or peptides into the analytical device 174 for analysis. An electrospray mass spectrometer (e.g. LCQ or Qtof) is designed to receive elution gradients from chromatography columns so that tube 158 can be coupled directly to the spectrometer. After elution, magnet 172 is slid up tube 158 and the beads 148 are released into a new vessel 176 containing a liquid 177 for reuse as shown in FIG. 22. If needed, a small amount of fluid (gas or liquid) may be pumped through the tube 158 to expel beads 148. As above, C18 coated beads for adsorbing peptide digests are preferred. The advantage of this apparatus is that one can capture all of t,he peptides in a digest and then deliver them all into a high sensitivity MS (electrospray) by using the C18 beads as a chromatography medium. While these C18 magnetic beads as a chromatography support may have a lower resolution than an equivalent size column packed with microparticulate C18 support, it has adequate resolution to separate the peptides from a digest of a protein prior to MS.

In this embodiment, the flow of eluting solution (which may be a gradient from a low percentage of eluent (e.g., 5% acetonitrile) to a higher percentage (e.g., 60% acetonitrile)) is delivered directly into the entrance to the electrospray mass spectrometer source. The gradual or stepwise elution of peptides from the beads can substitute for the reverse phase column chromatography step conventionally employed prior to ES-MS analysis of peptides and proteins. Beads can be re-used after extensive washing to remove any remaining peptides.

Alternative structures and designs can be used to capture the beads. For example, an electromagnet or permanent magnet can be attached to one side of the tube to retain the beads in the tube. With an electromagnet, the frit 168 can be omitted if the magnetic force is sufficient to capture beads 148 as the solution is aspirated through tube 158. Capture and release of beads 148 is performed by turning the electromagnet on and off. Furthermore, the design may be modified so that the capture apparatus is not moved to the analytical device or other treatment stage but rather placed in a vessel of elution solution and then aspirated through liquid tube 158 to be directly pumped into the analytical device. If a gradient is needed, multiple vessels of differing elution solutions may be used or a gradient maker may slowly change the gradient in the elution solution vessel.

As with the other apparatus above, multiwell plates may be used for simultaneously handling many samples. Preferably, each of the capture apparatus is robotically operated and controlled by a computer appropriately programmed to monitor and adjust for the number and type of different samples.

In another embodiment, beads with immobilized specific antibodies are used to capture an appropriate protein ligand and other proteins in the sample that interact with the ligand through other sites than the antibody binding site. If polyclonal or oligoclonal antibodies are used that are directed to many epitopes on the ligand protein, then other proteins interacting with the ligand protein may be recovered. The set of bound proteins includes the ligand and other proteins specifically associated with it. This mixture is likely to have many fewer components than the original sample (which may be a cell lysate), and may thus be amenable to analysis using conventional analytical techniques such as mass spectrometry (e.g., after digestion by passage over immobilized trypsin), or by one-dimensional electrophoresis (e.g., SDS gel electrophoresis), or by 2-DE. The information obtained (what proteins interact with the ligand) can be very useful, particularly when this information is obtained for many proteins in parallel (using a series of specific bead preparations). The associated components also have desirable properties by themselves and may be separately recovered and used as a method for producing, purifying or extracting one or more associated components.

In another embodiment, beads carrying immobilized proteins are used to recover other proteins from a mixture that specifically interact with the immobilized protein. In the preferred embodiment, the immobilized protein is bound to the bead by an extended linker arm. The immobilized protein can be renatured to recover its native structure by treatment with one or more steps including exposure to chaotropes (e.g., guanidinium hydrochloride) with subsequent gradual chaotrope removal, chemical disulfide reduction and gradual re-oxidation, or exposure to enzyme such as protein disulfide isomerase that can assist in re-formation of native disulfide bonds. Procedures for renaturation of SDS-denatured proteins are well known in the art, and any of these can be applied to beads carrying a bound denatured protein. If the protein is successfully renatured, it can act as a capture reagent to recover other proteins in a protein complex.

Beads carrying an immobilized protein, either denatured or renatured, can be used to selectively bind antibody moieties expressed on the surface of suitable bacteriophages, as employed in well known phage display antibody selection methods. A particular advantage of using protein "antigens" recovered from 2DE gels and immobilized on magnetic beads is that multiple cycles of binding and multiple cycles of sequential selection can be accomplished with the very small amounts of protein recovered from analytical or supporting 2DE gels.

Another embodiment of the present invention is to isolate a protein, previously found by 2DG, by affinity binding. This method generates an antibody by in vivo or in vitro immunization or by using the bead immobilized protein to adsorb a receptor, from serum, pooled antibody compositions, mixed antibody display phage, or other combinatorial library. The bead itself may serve as a carrier, adjuvant or modified to enhance the immunization process. The antibody or receptor is then immobilized on a different magnetically responsive bead. Commercially available Protein A (or Protein G) immobilized paramagnetic beads are preferred for immobilizing the antibody. The C18 (or the like) coated beads may also be used if a blocking agent is added after the peptides are bound.

This antibody or receptor-coated bead is then contacted with a biological sample containing a native protein, such as tissue or cell homogenates or a fluid, e.g. serum, to specifically adsorb the native protein. The protein is then eluted by an acidic buffer, ~pH 2.5, or other elution solution (ammonium thiocyanate, etc.) and the protein recovered. If needed, renaturing protocols may be used. By manipulation of the magnetically responsive beads repeatedly through adsorption, wash, elution and second wash vessels, the re-cycling permits slow but consistent recovery of the native protein for a number of uses. If carryover is small, one or more wash steps may be eliminated. Because the process is similar for any protein, optimization is easier and does not require knowledge of the protein's biological activity. This avoids much of the conventional protein purification and assay procedures that are completely different for each protein. Beads first coated with a protein followed by binding to a receptor with several binding sites may be used. Alternatively, receptor and ligand may be cross linked where permanent attachment is desired.

This affinity procedure of the present invention separates the protein of interest, other subunits, associated proteins, protein complexes, cofactors, substrates, and receptors that bind to the proteins. Later separation of the proteins provides more information and may be used as a method for separating and optionally identifying the substances bound to the protein of interest. Furthermore, while originally only one form of the protein may have been isolated, the receptor-coated bead may bind to other isoforms or alleles of the antigen, or protein variants that can then be analyzed and identified. A protein variant may differ by glycosylation, splicing, post translational cleavage, phosphorylation, etc. Each "protein variant" may have plural uses as well.

The protein-coated beads have numerous comparable uses for purifying protein binding factors, antibodies, and other receptors from a solution. As above, this protein-coated bead (also blocked) is contacted with a receptor containing biological sample, such as tissue or cell homogenates or a fluid, e.g. serum, hybridoma supernatant, phage display etc., to specifically adsorb the receptor present. The receptor is then eluted by an acidic buffer (if an antibody), ~pH 2.5, or other elution solution (ammonium thiocyanate, etc.) and the receptor recovered. If needed, renaturing protocols may be used. By manipulation of the magnetically responsive beads repeatedly through adsorption, wash, elution and second wash vessels, the re-cycling permits slow but consistent recovery of the receptor for a number of uses. If insufficient carryover occurs, one or more wash steps may be eliminated. Because the process is similar for any receptor, optimization is easier and does not require knowledge of the protein's or the receptor's biological activity.

The protein-coated beads are also used for determining and/or purifying a receptor from a combinatorial library of compounds or receptor display microorganisms or cells. As such, the beads provide a solid phase substrate for separation. Of particular concern are antibody display phage libraries constructed from immunoglobulin sequences obtained from naive animals or from animals that have been immunized to the protein or a mixture of proteins. The phage which bind to the beads may be later eluted and cultured to produce large quantities of protein binding receptor.

The receptor-coated beads may also be used for binding to and recovering naturally occurring components bound thereto. During two-dimensional electrophoresis, the protein may be denatured causing it to separate from other subunits, associated proteins, cofactors, protein complexes, substrates, membranes, etc. Using the cycling concept above, finding protein receptors for signal proteins, cytokines, membrane bound proteins, and the like may be achieved. Membrane bound proteins are notoriously difficult to isolate by conventional protein purification techniques. However, with the present invention, one may capture membrane bound proteins by their binding to protein coated beads. For such a method, it is preferable to use renatured proteins or to undergo an optional renaturation step. The recovered binding components may then be eluted from the protein-coated bead and identified by conventional means such as being digested to peptides for MS identification. The identification of associated components to the protein of interest is of particular importance in determining the biological properties of it.

Figure 23:
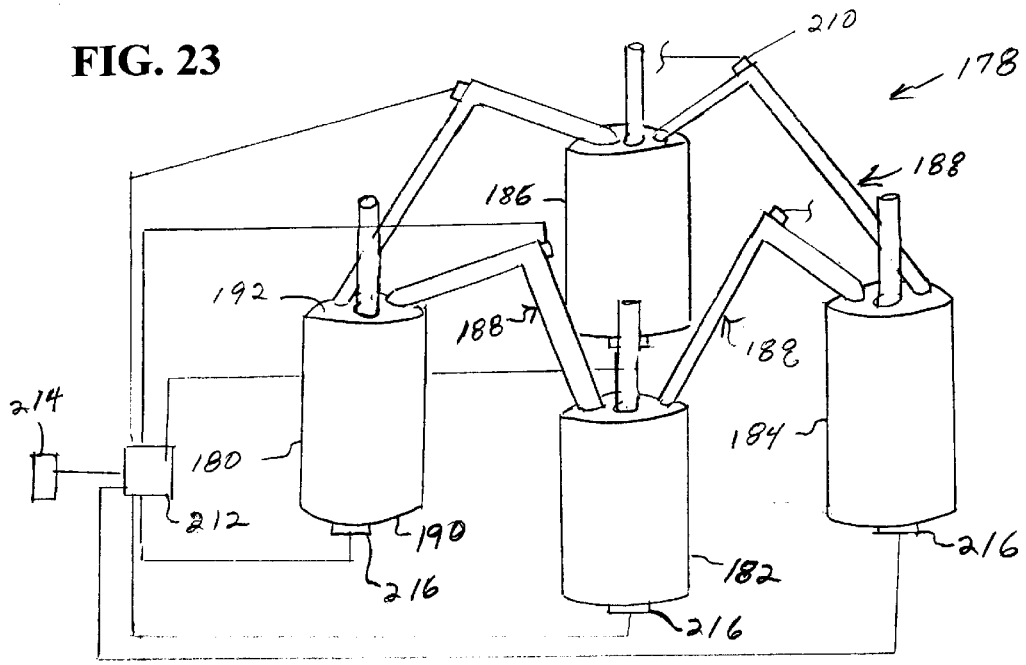
FIG. 23 is a perspective view of the separation apparatus in a fifth embodiment of the invention.
Figure 24:
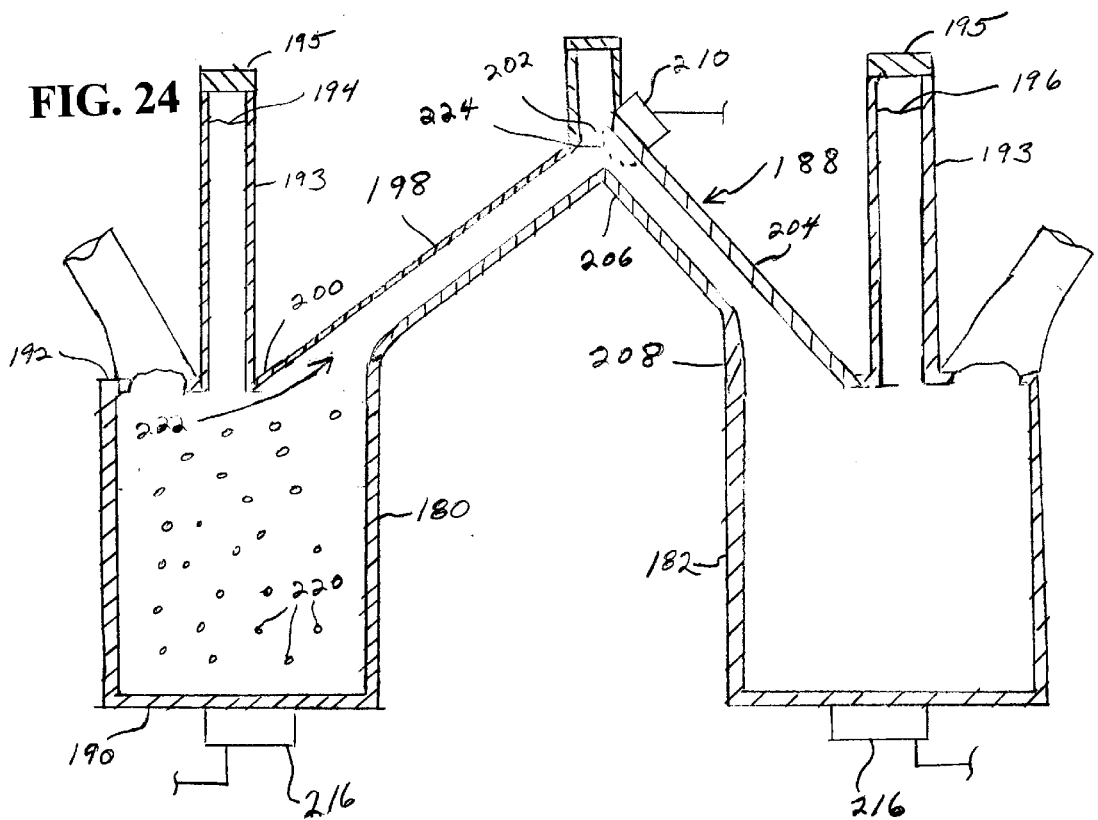
FIG. 24 is a partial cross-sectional side view of the apparatus of FIG. 23.

Embodiment of FIGS. 23 and 24

In this embodiment, the magnetically responsive beads are manipulated by controlled electromagnets or movable permanent magnets to move the beads between four vessels in a repetitive cycle. In the embodiment shown, the vessels are sample, wash, bound species accumulator and second wash vessels. The beads carry a protein (or other receptor) immobilized on them by an interaction (preferably covalent), which is not disrupted, by the conditions of the bound species accumulator. When the beads are dispersed in the sample vessel, one or more proteins or ligands are reversibly bound to them through specific interactions (e.g., antigen-antibody interactions or the interactions between subunits of a macromolecular complex).

The beads are then collected by the magnetic probe and transported to a wash vessel, where they are dispersed and any nonspecific carryover from the sample is effectively removed by dilution. Next, the beads are collected and transported to the bound species accumulator, in which the solution conditions are such as to promote release of the bound protein ligands into the solution (e.g., pH 2.5 or 2M ammonium thiocyanate). Finally, the beads are washed in a second wash step to return them to a condition suitable for binding ligand again. This cycle is repeated as many times as desired to accumulate the necessary amount of ligand in the bound species accumulator, or until the binding species is exhausted in the sample.

Stirring or ultrasound-based mixers, a changeable magnetic field or movable magnetic field may be used to enhance the mixing of the beads with these solutions between movements. The bound species accumulator vessel may also serve as a quantitative readout cuvette in which a measurement of bound species amount is made. In this case, the bound species is treated as the analyte, and is preferably labeled with a detectable label such as a fluorescent moiety. Until the ligand is exhausted in the sample, the amount of label detected in the bound species accumulator will increase after each cycle.

One suitable apparatus for performing the cycling extraction and accumulation of either binding members with movable beads is depicted in FIGS. 23 and 24. The apparatus 178 comprises four vessels, 180, 182, 184 and 186 each connected by tubes 188. The vessels are arranged in a circular fashion with tube 188 extending between adjacent vessels.

Vessels 180, 182, 184 and 186 in the illustrated embodiment are substantially identical. As shown in FIGS. 23 and 24, vessels 180 and 182 are connected by a connecting tube 188. Vessel 180 as shown has a substantially cylindrical shape with closed bottom wall 190 and a top wall 192. Vessels having other shapes can also be used. In the embodiment illustrated, vessel 180 includes a column 193 having an opening receiving a closure member 195. Vessel 180 contains a mixed antibody solution 194 and vessel 182 contains a wash liquid 196. In this embodiment, vessel 184 contains an elution solution and vessel 186 contains a wash solution. The solutions can be supplied by a pipette or supply tubes through the opening in each respective vessel.

Connecting tube 188 in the embodiment of FIGS. 23 and 24 include a first section 198 having a first end 200 coupled to vessel 180 and a second end 202 spaced from first end 198. A second section 204 has a first end 206, coupled to second end 202 of first section 198 and a second end 208 coupled to vessel 182. Sections 198 and 204 are joined to form an angle such that each section extends in a generally upward incline with respect to the respective vessel. Section 204 includes a magnet 210 attached at first end 206. Preferably, magnet 210 is an electromagnet connected to a power source 212 having a control 214 to selectively actuate magnet 210. Magnet 210 in alternative embodiments can be a ring shaped magnet surrounding tube 188. Each vessel includes a magnet 216 on the bottom wall that is also connected to power source 212 and control 214.

Magnetically responsive beads 220 are initially placed in vessel 180 containing an antibody solution as shown in FIG. 24. Beads 220 are retained in vessel 180 for sufficient time to enable the antibodies to bind to beads 220. In preferred embodiments, liquids 194 and 196 fill the respective vessels to a level so that tube 188 is filled with liquid. Beads 220 are transferred to the adjacent vessel by actuating magnet 210, which draws beads 220 from solution 194 and through first section 198 of tube 188 as indicated by arrow 222. Beads 220 drawn toward magnet 210 where the beads are captured in second section 204 of tube 188 indicated at 224.

Magnet 210 is then deactivated to release beads 220 and allow beads 220 to fall by gravity through second section 204 into the adjacent vessel. Magnet 216 in the bottom of each vessel can be actuated as needed to pull beads 204 downwardly into the vessel. Each vessel can also include a mixing device such as an impeller, stirring bar, ultrasound source, or the like.

In further embodiments, tubes 188 can have a gently curving shape or can have a recess to retain the collected beads. Alternatively, tubes 188 can be straight and extend directly between adjacent vessels. Suitable valves or a flow restricter can be included in the tubes to control the flow of liquids and beads between adjacent vessels. A magnet, such as a ring shaped magnet, is positioned around the tube to transfer the beads from a vessel into the tube.

The magnets 210 and 216 are adjustable as to their relative magnetic force exerted by altering the electric current. When permanent magnets are used, the vessel and/or magnet can be shielded or the magnets can be moved toward or away from the vessel. If the beads are highly charged, electrodes contacting the solution may be substituted for magnets as the mechanism for moving the magnetically responsive beads through the liquid filled tubes.

In the illustrated embodiment, beads 220 are paramagnetic and have antigen bound thereto to isolate and accumulate monospecific antibody from a mixed antibody source. It will be appreciated that the reverse for each combination can be used. Beads 220 are directed in a sequential fashion through each vessel. At the end of the process, the monospecific antibody is recovered from vessel 184. The fluid levels in each vessel remain below the junction with tube 188 and can differ in different vessels. Alternatively, the entire system can be filled with a dense or viscous fluid to reduce or substantially eliminate fluid transfer between adjacent vessels. In further embodiments, the connecting tubes can have a very small diameter or include valves to control fluid transfer between adjacent vessels.

The beads may be in less than all of the vessels, although typically each vessel will contain beads during the process. Since each vessel performs a different reaction, each vessel can be of different size, shape, and temperature. The needs of each reaction may require the fluid to be changed frequently (such as a wash fluid) independently through the opening. The liquids can be changed continuously through lines to outside apparatus (not shown). If fluid is exchanged while beads are present, steps should be taken to prevent beads from being lost such as filtering out the beads, sedimenting or attracting the beads away from the outlet.

The apparatus is useful for a wide variety of other industrial processes including extractions, chemical synthesis (e.g. peptide or oligonucleotide synthesis, combinatorial chemistry, etc.), DNA amplification (e.g. different vessels have different nested primers), and article processing. One or more of the wash stations can be removed depending on the process being performed and an allowable amount of carryover.

Embodiment of FIGS. 25–28

Figure 25:
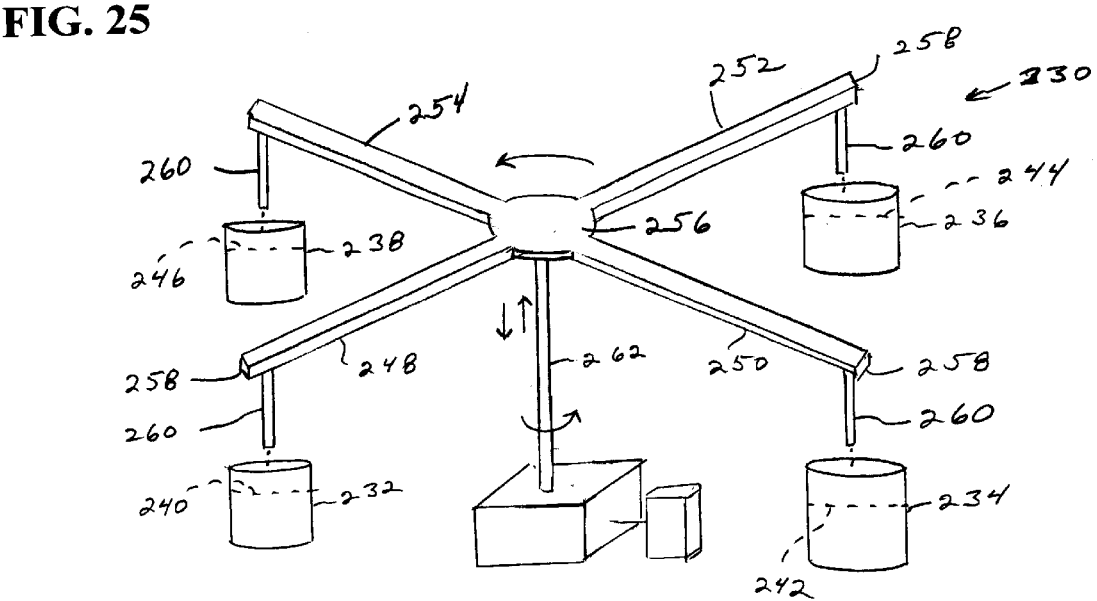
FIG. 25 is a perspective view of the bead manipulation device in another embodiment, of the invention showing four arms mounted on a rotating and reciprocating shaft.

In another embodiment of the invention shown in FIGS. 25–28, a manipulation device 230 for transferring magnetically responsive beads between vessels 232, 234, 236 and 238 is shown. As in the previous embodiment, vessel 232 contains a sample liquid 240 having a target component dispersed therein. Vessel 234 contains a wash liquid 242. Vessel 236, contains an eluting agent 244 and vessel 238 contains a wash liquid 246. As shown in FIG. 25, vessels 232, 234, 236 and 238 are arranged in a circle.

Manipulation device 230 includes four arms 248, 250, 252 and 24 extending radially outward from a hub 256. Each arm has an outer end 258 having a magnetizable probe 260. In the embodiment illustrated, probe 260 is an electromagnet.

Figure 26:
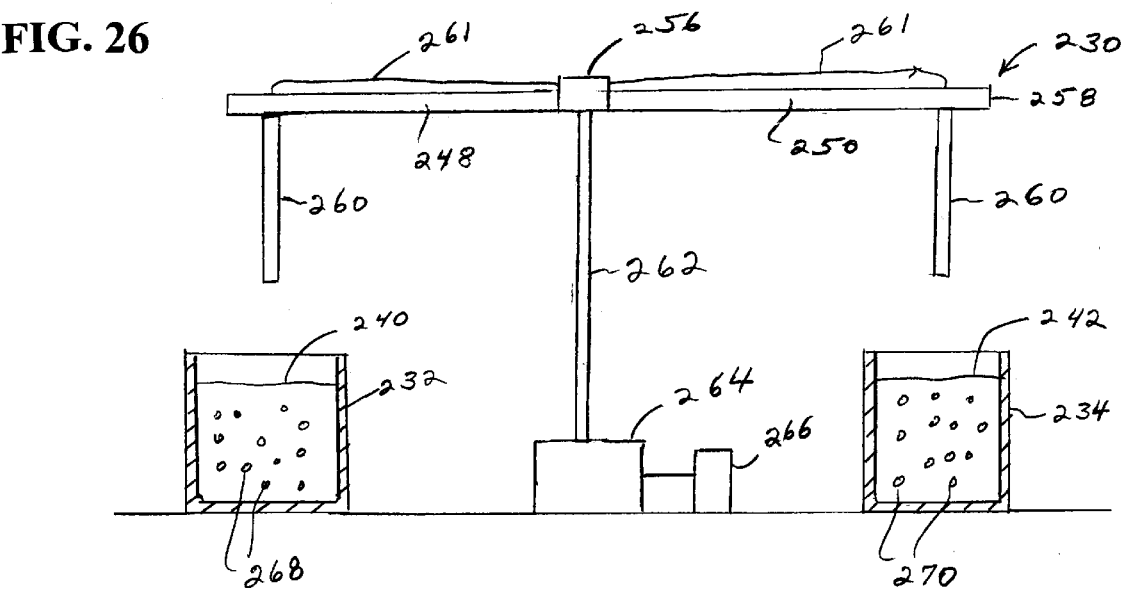
FIG. 26 is an elevational front side view of the device of FIG. 25 showing magnetizable probes in a retracted position.

Hub 256 is supported on a shaft 262, which is coupled to an operating device 264. In one embodiment of the invention, operating is a step motor capable of rotating shaft 262 and the arms to a predetermined position. Shaft 262 is also mounted for reciprocating movement in an axial direction of shaft 262. A control device 266, such as a computer or microprocessor for controlling the movement of operating device 264 and magnetizing probes 260. As shown in FIG. 26, wires 261 extend from probes 260 to control device 266.

In the embodiments of the invention, a vessel 232 contains sample liquid 240 as shown in FIG. 26 and vessel 234 contains a wash liquid 242. An amount of magnetically responsive beads 266 are placed in vessel 232 and an amount of beads 268 are placed in vessel 234. It will be appreciated that a similar amount of beads (not shown) are added to vessels 236 and 238. As in the previous embodiments, beads 266 and 268 have a coating of a material having a binding affinity for the target component.

Figure 27:
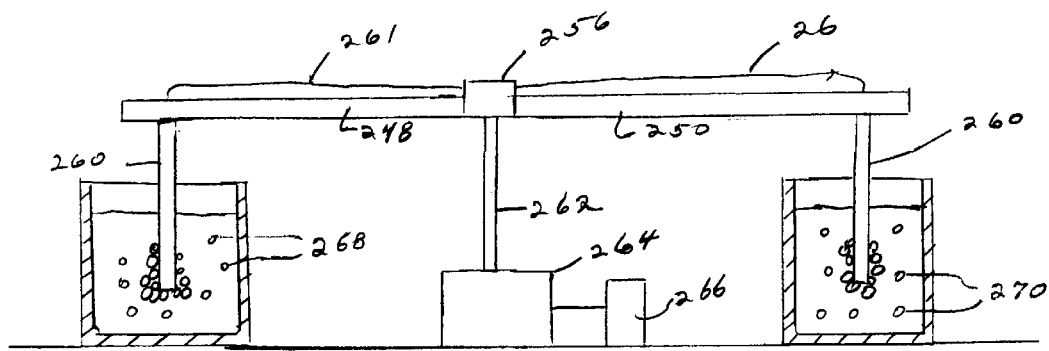
FIG. 27 is an elevational front side view of the device of FIG. 25 showing the magnetizable probes inserted in the vessels.
Figure 28:
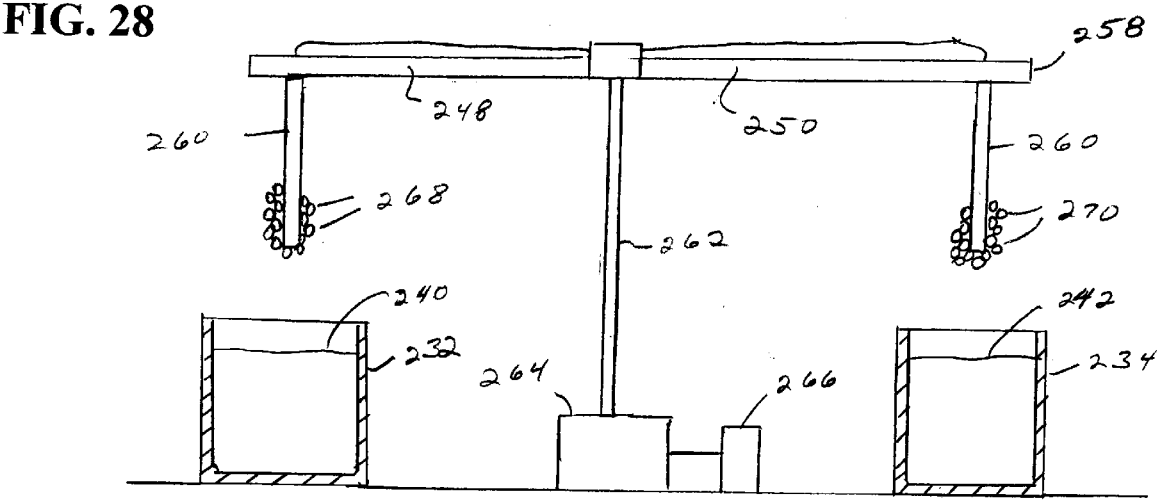
FIG. 28 is an elevational front side view showing the probes retracted with the captured beads.

Referring to FIGS. 26 and 27, beads 268 are dispersed in sample liquid 240 in vessel 232 for sufficient time to bind with the target components. Beads 270 are dispersed in wash liquid 242. Operating device 264 is actuated to lower probe 260 of arms 248, 250, 252 and 254 into the respective vessel 232, 234, 236 and 238. Probes 260 are magnetized as shown in FIG. 27 to capture beads 268 and 270. Shaft 262 is raised to the position shown in FIG. 28 to retract probes 260 from the respective vessel. Shaft 262 is then rotated in the direction of arrow 270 shown in FIG. 26 to orient the probes 260 above the adjacent vessel in the series. In this manner, beads 268 having the captured target component are transferred to the wash vessel 234 by lowering shaft 262 to insert probe 260 containing beads 268 into wash solution 242. Probes 260 can be demagnetized to allow the beads to disperse in the respective liquid. Probes 260 are again magnetized to capture the beads and transfer the beads to the adjacent vessel.

As shown in FIG. 25, device 230 is able to transfer the beads sequentially from sample vessel 232, wash vessel 234, eluting vessel 236 and wash vessel 238. Continuous operation of device 230 recycles the beads from wash vessel 238 back to sample vessel 232 for again capturing the target compound. The target compound eluted in vessel 236 is recovered and analyzed according to standard procedures.

In the invention, a small amount of protein antigen can be used to make 1000 fold more antibody molecules, by running 1000 cycles through the apparatus 178. The antibody can be purified, immobilized and run through a similar apparatus to make 1000 fold more protein molecules and this protein may then be used to make another 1000 fold more antibody, and so forth. The essence of this approach is that very small amounts of either protein or antibody (e.g. the protein from a 2-D gel, or any other micro analytical method) can be used to bootstrap a large amount of the pure protein without starting with a pure antibody. This permits the use of a pool of mixed antibodies or other receptors such as commercial gamma globulin, antibody display phage, combinatorial chemicals etc. Alternatively, from a small amount of antibody, and a mixture of proteins (such as a cell lysate) much larger amounts of pure protein and monospecific antibody can be made by recycling and by "ping-ponging" between antigen and antibody approaches.

The importance of using the movable beads is that very small levels of starting material are required. It would be impractical and perhaps not possible, to make and run small affinity columns for the initial stages where material is minimal. The amount of binding partner recovered in each step is minimal and dissolved in a large volume of liquid for each cycle. By contrast, the bead approach concentrates the binding partner in a minimal volume of liquid, which enables use of cycling for small quantities of initial ligand or receptor. Furthermore, with beads, this cycling protein amplification in parallel can be performed for many proteins and/or antibodies at once with a goal of making antibodies quickly to many antigens or many antigens to micro amounts of antibody. This system is also a substitute for the preparation of monoclonal antibodies, since a large supply of antibodies can be made much more quickly than traditional methods for making monoclonal antibodies. Generally, a few hours is required for large scale production of antibodies and antigens for monoclonal antibody production. The proteins and monospecific antibodies so prepared may be used for the same varied in analytical, medical and industrial uses as other conventionally prepared proteins and antibodies.

Where the antibody is not monospecific due to a contaminant or other reason, the final product will be specific to only a few antigens. Conventional immunosubtraction techniques can be used if the antibody is not monospecific.

One exemplified protocol is to produce large quantities of antibody for diagnostic or therapeutic uses, starting with only very small quantities of protein or peptide, perhaps from a two-dimensional electrophoresis gel spot or even a fragment of a protein. First, one immobilizes the protein on the magnetic beads as described above followed by an optional renaturing step. Then a non-specific pooled receptor source(s), commercial gamma globulin, antibody display phage, combinatorial chemistry products, etc., is contacted to adsorb these receptor(s). The receptors are suitably eluted, for example by a citrate buffer, pH 2 and the recovered receptors are then immobilized on beads, preferably magnetic beads to form receptor beads. Previous or post biotinylation of the receptor is preferred for use with avidin/streptavidin beads or biotinylated beads with free avidin/streptavidin. The receptor beads are then used to adsorb native protein, which may be complexed with other proteins, from a biological sample (repeatedly) that may then be eluted to produce large quantities of native protein. Large quantities of native protein may then be used to produce large quantities of specific receptor by immunization of an animal, in-vitro immunization, adsorption of antibody from gamma globulin, convalescent serum, pooled biological fluids, hybridomas, antibody display phage, combinatorial compounds, etc. In this last step, the native protein may be immobilized on magnetic beads or any other solid phase if desired.

In one embodiment of the invention, a biotin-conjugated 2-DE separated protein (such as human serum protein SAA) is immobilized on streptavidin-coated magnetic beads, and cycles the beads through a sample containing antibodies to SAA (and potentially to many other antigens). Antibody specific to SAA is recovered in the bound species accumulator, separate from antibodies of all other specificities, which remain in the sample or in the first wash.

In another embodiment, a specific antibody is prepared against the desired ligand (e.g., human serum protein SAA) and this antibody is covalently coupled or otherwise tightly bound to magnetic beads. The antibody may be, for example, the one purified in the preceding paragraph. The objectives of this system are 1) to allow a small amount of antibody to be used to accumulate a stoichiometrically much larger amount of analyte through cycling, 2) to allow a wide dynamic range of detection by continuously monitoring analyte accumulation during cycling, and 3) to provide a means of using the recycled beads for multiple samples.

A ligand-containing sample is reacted with a general-purpose fluorescent protein labeling reagent, such as commercially available activated Cy3 (Amersham Pharmacia Biotech), so that all proteins are labeled with the dye, preferably stoichiometrically. The sample and beads are then placed in a suitable 4-chamber device, and controllable electromagnets, are used to move the beads into the sample, where fluorescently labeled ligand binds to the beads. A mixing means, e.g. stirrer, changing magnetic field, etc. may be used to help expose the beads to the sample. A magnetic probe then moves the beads into a wash to remove any protein not bound tightly via an antigen-antibody interaction, and then the beads are moved into the bound species accumulator chamber where acid pH (e.g., pH 2) causes the ligand to be released from the antibody bearing beads. The beads are then moved to a wash chamber (pH 7) and subsequently back to the sample to capture more ligand. A single wash station may be used for both wash steps if it is frequently refreshed with clean wash solution, resulting in a three station system.

Instead of moving the beads to other vessels, one may collect the beads and aspirate, wash and change the solution in the same vessel for performing the next step.

During the period when the beads are not in the bound species accumulator chamber, an optical system measures the amount of dye in that chamber. A suitable example is the fluorescent dye Cy3 and a corresponding fluorescent optical system though other chemical signals detected by other non-optical means may be used. In general, the signal (or the components that generate the signal) must be stable under the conditions in the accumulator, or else must be recovered by changing the conditions in the accumulator. Fluorescein is not fluorescent at pH 2.5, for example, and thus this label is not suitable for use in a system in which the accumulator is to be monitored without further addition s of pH neutralizing reagents. Each cycle transports more labeled ligand to the elution/accumulation chamber and thus the signal increases by a certain amount after each elution cycle. If ligand begins to be depleted in the sample, the increases in signal will taper off to an asymptote. If a large amount of ligand is contained in the sample (and the fluorescence thus increases by a constant amount each cycle) then the cycle time (or more specifically the time spent by the beads in the sample) can be reduced to transport an amount of analyte less than the saturating amount on each cycle. The amount of ligand transported from the sample to the elution/accumulation chamber will depend on the quantity of antibody on the beads, its affinity for ligand and the amount of ligand in the sample. The recycling nature of the system allows one to use less antibody on the beads than would be required to capture all the ligand present. Cycling, with readout periodically or after each cycle, also allows better quantitation of the analyte because the resulting curve of signal vs. cycle can be smoothed and otherwise analyzed to determine the parameters of the capture system. Under certain conditions, such as changes in pH, undesirable changes can occur in the protein, such as denaturation of antibody. Elution can be effected by providing a flow of a small amount of an acid solution over the probe. The acid solution drips into a bound species accumulator where it is diluted rapidly by a concentrated neutral buffer.

In one embodiment, the four chambers can be a sample well in a specific position in a multi-well plate (e.g., a 96-well plate), a wash position in a second plate, a bound species accumulator well in the same position in a third plate, and a final wash position in a fourth plate. Using 96 different magnetic bead preparations, carrying 96 different receptors or proteins, 96 such cycling assays can be carried out in parallel using a 96-probe magnetic bead transport and four 96 well Microtiter plates. After release of bound species on each cycle, the bound species accumulator plate can be read in a conventional fluorescent plate reader. Alternatively, the 4 chambers can be 4 wells of a single multi-well plate, 4 different 96 well sections of a 386 well plate or a different number plate depending on the number of samples.

It will be appreciated that the apparatus of the invention is equally applicable to many other cycling reactions or to other multistep procedures such as the purification of cofactors, associated proteins, substrates, receptors, products, DNA amplification by PCR, nucleic acid extraction, solid phase chemical synthesis, analytical system (for immuno and other binding assays), etc. The apparatus may be viewed as a self contained laboratory or even large scale production facility. The apparatus is preferably a "lab on a chip" module which is inserted into an automatically controlled machine which is computer controlled and robotically manipulated where the bead movement by application of magnetic forces determines the reaction of the moment.

The protein-coated beads and the receptor-coated beads of the present invention have many uses in analytical measurements. In immunohistochemistry, one can detect a ligand or receptor on the slide by using the coated beads above alone or more preferably using a labeled bead or pre-labeled component bound by the bead. U.S. Pat. No. 5,395,688 is a way to fluorescently label the beads. The results are easily observable under a microscope. Plural different protein or receptor-coated beads may be used simultaneously. It is preferable to have different colored or different labeled beads for easy identification. The receptors or proteins may also be separated from the bead, and used by conventional techniques either indirectly or labeled and used directly in immunohistochemistry.

The present invention is particularly amenable to robotic manipulation on a large scale. Typical two-dimensional gels may have hundreds to thousands of different protein spots. Each may be cut from the gels by a number of commercially available systems or a modified colony picker and the steps performed in parallel. A robotic device may be built from a modified 96-well plate system where a second arm (or a separate portion of the dispensing and aspirating arm) contains a magnetic probe.

Example 1: Preparation of Protein Coated Beads

A sample of human serum was separated by 2-D electrophoresis followed by Coomassie Blue staining according to the ISO-DALT® System Anderson, et al, Anal. Biochem. 85: 331–340, (1978) and Anderson, et al, Anal. Biochem. 85: 341–354, (1978) and Two-Dimensional Electrophoresis: Operation of the ISO-DALT® System Leigh Anderson, 1988, Large Scale Biology Press, Washington, D.C., Library of Congress catalog Card No. 88-80097, ISBN 0-945532-00-8. The spot corresponding to the light chain of haptoglobin (a protein comprised of both heavy and light chain components) was excised from the 2-D gel, by cutting out a cylindrical plug 1–2 mm in diameter, and of a length equal to the thickness of the gel (1.5 mm). The excised spot is washed three times in 200 $\mu$l of 50% acetonitrile in water with ultrasonic agitation to remove the Coomassie Blue stain. The gel spot was excised based on its location on the standard map of human plasma proteins (Anderson & Anderson, Proc Natl Acad Sci USA 74(12):5421–5 (1977) and Anderson & Anderson, Electrophoresis 12(11):883–906 (1991).

The resulting destained protein spot was washed twice in 200 $\mu$l of 0.5 M sodium carbonate buffer pH 8 (30 min each) and then placed in 50 $\mu$l of 1 mg/ml NHS-LC-LC-biotin labeling reagent system (Pierce Product No. 21343) in sodium carbonate. The reaction was allowed to proceed for 39 min at room temperature, and then a further 100 $\mu$l of 0.1 M ethanolamine was added to combine with any unreacted biotinylation reagent. After a further 30 min, the spot was washed 3 times (30 min each) in 0.1% SDS in tris-glycine buffer.

An electroelution device as shown in FIG. 1 was assembled using a 200 $\mu$l "yellow" Eppendorf pipette tip plugged with 2 $\mu$l of 10%T polyacrylamide gel containing elution buffer. Dynal paramagnetic microspheres coated with streptavidin were added to the pipette tip (10 µl of a 10% slurry, yielding a 1 µl packed bed after the beads were collected at the bottom (atop the plug) by means of a magnet. The spot was placed in the tip and allowed to settle to a point at which it was wedged into the cone of the tip. Finally, the tip was suspended in a small beaker of elution buffer, and platinum wire electrodes placed in the tip and in the beaker. A current of 50 V was applied for 30 minutes to elute the protein, and capture the protein on the beads. After elution, the apparatus was disassembled, the gel piece removed, and the paramagnetic beads collected by magnetic attraction and placed in one well of a 96-well plate containing 200 µl phosphate-buffered saline with 0.1% fish skin gelatin (PBSG).

Using an external magnet placed against the outer surface of the vessel to capture the beads, the beads are washed successively in 5 wells containing 200 µl of a wash liquid. The beads are washed by introducing the beads into the wash solution, releasing the beads, shaking the plate to disperse the beads, incubation for 1 minute, and recapture of the beads with the magnet. The wells can be the wells of a 96-well plate. The wash liquid is phosphate-buffered saline with 0.1% fish skin gelatin (PBSG).

Example 2: Renaturing of Protein

The protein on the beads is renatured by transporting the beads through a series of buffer solutions having a concentration of about 8 M urea, 1% mercaptoethanol plus a buffer used along in increments of 0.5 M urea. Each stage involves an incubation period of 15 minutes at 37° C., followed by withdrawing the beads with the probe and transporting them to the next vessel.

Example 3: Preparation of Antibodies and Proteins

The beads of Example 1 ("antigen-coated" beads, the beads of Example 2 may be used also) are next introduced into a well containing a polyclonal antiserum to human haptoglobin, and dispersed to allow binding for 1 minute. Next, the beads are removed via a probe, and washed twice in separate wells containing 200 µl PBSG for 1 minute at 25° C. temperature. Finally, the beads are introduced into a well containing 0.9% NaCl plus HCl pH 2.5 for 1 minute at 25° C. temperature. This treatment releases the bound anti-haptoglobin antibodies into the medium.

Following release, the beads are removed with a probe. The probe is a "KingFisher" (Labsystems OY, Helsinki, Finland) (previously used for mRNA purification) modified by adding a plastic collar. 50 µl of a pH 8 buffer concentrate is then pipetted into the well and mixed, raising the pH to 8. Next 10 µl of a 10% suspension of paramagnetic beads coated with Protein G is introduced into the well and incubated with agitation for 6 hours. The antibodies are covalently crosslinked to the protein G using dimethylpimelimidate (Gersten et al, Journal of Immunological Methods 127:215–220 and Schneider et al, Journal of Biological Chemistry 257:10,766–10,769), resulting in a second set of "antibody-coated" beads. Following crosslinking to immobilize the anti-haptoglobin antibodies on these beads, they are transferred to a well containing 200 µl of normal human serum, and agitated for 10 min to allow binding of native haptoglobin. The antibody-coated beads are then washed by transferring them in succession through three wells containing 200 µl PBSG using the magnetic probe.

The beads are finally transferred into a small volume of 5% acetic acid to elute the native haptoglobin from the beads, and the beads removed. The haptoglobin in solution is divided into two aliquots: about 10% of the material is mixed with a solution of MALDI matrix (α-cyano-4 hydroxycinnamic acid saturated in 40% $CH_3CN$, 0.1% trifluoroacetic acid (TFA) in water) and spotted onto a MALDI mass spectrometer target (Voyager DE-STR, PE Biosystems) and analyzed to reveal both heavy and light chains. The remaining 90% of the eluted native haptoglobin is mixed with 2-D gel sample buffer and analyzed by 2-D to reveal both heavy and light chains of haptoglobin with no appreciable contamination by other serum proteins.

Examples 1 and 3 demonstrate the use of material purified by 2-D gel and immobilized on paramagnetic beads to isolate specific antibody from a polyclonal antiserum. This antibody is subsequently used to capture native antigen from serum, also determining what other subunits (in this case the heavy chains) are combined with the 2-DE gel isolated light chains in the native state.

Example 4: Preparation of Antibody and Assay by Cycling

The antigen-coated beads prepared in Example 1 are exposed to an aliquot of the same polyclonal antiserum to haptoglobin, after the antiserum have been fluorescently labeled by treatment with Cy3 (from Amersham), and the unreacted Cy3 removed. In this antiserum, essentially all the proteins (including the antibodies) are simultaneously fluorescently labeled by this procedure.

Some of the antibodies are isolated with the beads by antibody binding to the beads. They are washed in PBSG, and the antibody eluted with acid as before. The amount of fluorescence in the transferred antibody is measured using a TECAN fluorescent plate reader in arbitrary units. Then the process is repeated with the same beads, with the antibody released into the same well, adding its fluorescence to that already measured. A new measurement showed increased fluorescence. This process is repeated a total of five times, resulting in the isolation (in the acidic elution well) of approximately 5 times as much antibody as can be bound by the antigen-coated beads in a single pass.

This example demonstrated that the beads can be recycled to produce more antibody than corresponds stoichiometrically to the amount of antigen on the antigen-coated beads or recovered from the 2-D gel.

Example 5: Immunohistochemical Staining

The fluorescently-labeled antibody isolated in Example 4 was neutralized and reacted with thin sections of normal liver tissue and normal kidney, extensively washed and examined under a fluorescence microscope equipped with excitation and emission filters suitable for detecting Cy3 fluorescence. The Cy3-labeled anti-haptoglobin antibodies bound to liver parenchymal cells (as expected since these cells produce haptoglobin), but did not bind to kidney cells (which do not contain haptoglobin).

The above method is repeated with the beads of Example 3, which are coated with polyclonal anti-haptoglobin antibody. Immobilization of beads on the liver parenchymal cells but not the kidney cells is indicative of accurate immunohistochemical staining.

This example demonstrates the use of antibodies isolated by the described method to identify the location of a protein in tissue sections.

Example 6: Screening of a Phage Display Library

The antigen-coated beads of Example 1 are exposed to an antibody phage display library constructed from naive human donors. The phages that bind to the beads are eluted and cultured to produce single chain antibody protein. An ELISA assay is constructed using this antibody and used to measure haptoglobin in a series of human sera.

Example 7: Identification of a Protein Spot

The method of Example 1 was repeated to the point where the protein gel spot is excised. The protein gel spot was destained by washing in 200 µl of water for two hours, followed by 40% acetone, 10% triethylamine and 5% acetic acid in pH 6.4 water for 30 minutes with shaking. The gel piece was then washed for one hour in 200 µl of water and 30 minutes in 50% acetonitrile. The gel piece was removed and air-dried for two hours. The gel piece was spotted with a solution of 3 µg trypsin in 300 µl 100 mM Tris-HCl pH 8.2 in 10% acetonitrile and incubated for 20 hours at 37° C. The peptides were extracted twice for 30 minutes each with 300 µl 60% acetonitrile, 0.1% trifluoroacetic acid at 37° C. 5 µl of 100 mM Tris-HCl pH 8.2 buffer is added followed by about 100 µg paramagnetic beads coated with C18 hydrocarbon with shaking for 30 minutes.

The magnetic probe of FIG. 2a is inserted and the beads withdrawn. The beads are dispersed into 500 µl of 100 mM Tris-HCl pH 8.2 buffer in a new tube and shaken for 30 minutes. The beads are again withdrawn using the magnetic probe, MALDI matrix solution containing 40% acetonitrile of Example 3 is prepared, and 2 µl is pipetted onto the magnetic probe at a location above the beads. Additional quantities of 2 µl are pipetted at approximately 30 second intervals until a droplet of fluid is seen collecting at the tip of the magnetic probe. A MALDI mass spectrometer target is then touched to the droplet to spot the MALDI target. Protein identification continued as in Example 1.

Example 8: Digestion of Proteins Captured on a Bead

Beads prepared as for Example 1 up to the point of washing in PBSG are further washed in deionized water and placed in a vessel with a solution of 3 µg trypsin in 50 µl 100 mM Tris-HCl pH 8.2 in 10% acetonitrile and incubated for 20 hours at 37° C. Peptide products are released into the liquid. The avidin coated magnetic beads are removed by a magnetic probe. $C^{18}$ coated magnetic beads are added to the liquid and incubated for 30 minutes. The magnetic beads are captured on a magnetic pin or probe. A 1 µl aliquot of MALDI matrix solution is dripped down the magnetic pin and the captured beads to elute the peptides onto a plate for MALDI mass spectrometry. When sufficient fluid flows to contact deposit liquid on a plate, additional 1 µl aliquots are added sequentially until a liquid is spotable on the plate.

Example 9: Introduction of Peptides Captured on a Bead Into an Electrospray Mass Spectrometer The method of Example 7 is repeated to the point where the magnetic probe of FIG. 17 is inserted. The magnetic beads, suspended in the peptide extraction liquid of the digestion well, are aspirated into a capillary tube (100 micron internal diameter) and come to rest against a frit placed 5 cm inside the tube of FIG. 17. While the beads are held in place by the in flowing liquid, a magnet is moved into position surrounding the capillary in the region filled by the beads. When all the extraction liquid has been aspirated, the aspiration ceases, the magnet continues to hold the magnetic beads in place in the capillary tube. Next, the capillary tube assembly is moved by a positioning device to aim into the inlet of an electrospray mass spectrometer (Finnegan, LCQ).

A gradient of 0 to 60% acetonitrile in 0.5% trifluoroacetic acid/water is delivered into the capillary tube, flowing out over the magnetic bead bed and into the mass spectrometer. Peptides are eluted progressively, inducted into the mass spectrometer and there characterized as to mass and fragmentation products in order to identify the protein. Finally, the capillary tube assembly is re-positioned over an empty well of a 96-well plate, the magnet is repositioned to a location remote from the packed beads, and a rapid outflow of liquid (1 ml/min) is delivered for 15 sec. to eject the magnetic beads in preparation for collecting the beads in the next digest well.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method of recovering a target component from a sample, said method comprising the steps of:

providing a solution containing said sample;

contacting said solution with an amount of magnetically responsive beads, said beads having an outer surface with a polymeric coating having pendant hydrophobic groups, said hydrophobic groups having a binding affinity for said target component, said beads being contacted with said solution for sufficient time to bind said target component to said beads; and recovering said beads from said solution.

2. The method of claim 1, wherein said target component is a protein or peptide, and said coating on said beads has a binding affinity for proteins or peptides.

3. The method of claim 2, further comprising washing said recovered beads with a washing liquid to remove unbound materials from said beads.

4. The method of claim 2, further comprising eluting said bound proteins or peptides from said beads.

5. The method of claim 2, wherein said magnetically responsive beads have a magnetizable core.

6. The method of claim 1, wherein said pendant hydrophobic groups are hydrocarbon groups.

7. The method of claim 1, wherein said pendant hydrophobic groups are $C_{18}$ hydrocarbon groups.

8. A method of recovering a protein or peptide from a sample, said method comprising the steps of:

providing a solution containing said sample;

contacting said solution with an amount of magnetically responsive beads, said beads having an outer surface with a polymeric coating having a binding partner with a binding affinity for said protein or peptide, said beads being contacted with said solution for sufficient time and under conditions for said binding partner to bind said protein or peptide to said beads, wherein said coating or said binding partner on said beads is reactive with said protein or peptide and forms a covalent chemical bond with said protein or peptide;

separating said beads from said solution; and cleaving said proteins or peptides from said beads.

9. A method of recovering a plurality of target components from a sample, said method comprising the steps of:

providing a solution of said sample containing first and second target components;

contacting said solution with an amount of first magnetically responsive beads comprising a coating with a specific binding affinity for a first target component, and an amount of second magnetically responsive beads having a coating with a specific binding affinity for a second target component, simultaneously contacting said beads with said solution for sufficient time to bind said first and second target components to said first and second magnetically responsive beads, respectively; and recovering said beads from said solution.

10. The method of claim 9, wherein said target component is a protein or peptide.

11. The method of claim 9, further comprising simultaneously eluting said first target component and said second target component from said beads.

12. A method of recovering a target component from a sample, said method comprising the steps of:

providing a solution and a support medium in said solution, said support medium containing said sample;

contacting said solution with an amount of magnetically responsive beads, said beads having an outer surface with a polymeric coating having a binding affinity for said target component, applying an electric current to said solution to cause said target component to diffuse from said support medium into said solution, said beads being contacted with said solution for sufficient time to bind said target component to said beads; and recovering said beads from said solution.

13. The method of claim 12, comprising applying a first electrode and a second electrode in said solution, positioning said beads and said support medium between said electrodes, and applying said electric current to cause said target component to diffuse toward said beads and attach to said beads.

14. The method of claim 13, wherein said beads are in the form of a bed, said method comprising positioning said bed of beads between said support medium and at least one of said electrodes.

15. The method of claim 13, comprising providing a permeable membrane between said electrodes, wherein said bed of beads is supported on said permeable membrane.

16. The method of claim 12, wherein said target component is a protein or peptide.

17. The method of claim 12, wherein said support medium is an electrophoresis gel.

18. The method off claim 17, wherein said electrophoresis gel is from a two-dimensional electrophoresis gel.

19. A method of recovering a target component comprising the steps of:

contacting a solution or dispersion of a target component with an amount of magnetically responsive beads having a coating with a binding affinity for said target component, said contacting step being for sufficient time for said target component to bind to said beads;

aspirating said solution or dispersion containing said beads through a tube having a filter device and collecting said beads on said filter device;

washing said beads inside said tube by passing a wash solution through said tube, and eluting said target component from said beads.

20. The method of claim 19, providing an electromagnetic field around said tube to retain said beads in said tube during said eluting step.

21. The method of claim 20, wherein said tube includes a magnet surrounding said tube for providing said electromagnetic field.

22. The method of claim 21, wherein said magnet is slidable on said tube, said method comprising sliding said magnet proximate said filter device during said eluting step.

23. The method of claim 20, further comprising transferring the tube to a second solution or dispersion of a target component after said eluting step, and deactivating said electromagnetic field to release said beads into said second solution or dispersion.

24. The method of claim 23, further comprising supplying a liquid through said tube to carry said beads into said second solution or dispersion.

25. The method of claim 19, wherein said filter member is a porous glass frit.

26. The method of claim 19, comprising:

inserting a first end of a tube into said solution, wherein said filter member is mounted within said tube; and aspirating said solution from a second end of said tube to collect said beads on said filter member.

27. The method of claim 26, further comprising subjecting said beads to an electromagnetic field to retain said beads in said tube and removing said electromagnetic field to separate said beads on said frit.

28. The method of claim 27, comprising inserting said tube into a wash liquid, deactivating said electromagnetic field to detach said beads from said tube and to disperse said beads in said wash liquid, activating said tube to induce said electromagnetic field and to reattach said beads to said tube, and removing said beads and said target component from said wash liquid.

29. The method of claim 28, wherein said eluting step comprises eluting said target component from said beads while said beads are attached to said tube.

30. The method of claim 29, wherein said eluting step comprises inserting said tube into an eluting solution, deactivating said tube to discontinue said electromagnetic field and disperse said beads in said eluting solution and elute said target component, activating said tube to produce said electromagnetic field to attached said beads to said tube, and removing said tube and beads from said eluting solution and eluted target component.

31. The method of claim 19, further comprising positioning an open end of said tube in an inlet of an analytical device; and eluting said target component from said beads retained in said tube directly into said analytical device and analyzing said target component.

32. A method of continuously recovering a target component from a liquid sample comprising the steps of:

providing a liquid sample containing said target component in a sample vessel and contacting said liquid sample with an effective amount of magnetically responsive beads having a coating with a binding affinity for said target component, said contacting step being for sufficient time to enable said target component to bind to said coating on said beads;

transferring said beads to an eluting vessel containing a liquid eluting agent and eluting said target component from said beads; and returning said beads to said sample vessel containing said liquid sample.

33. The method of claim 32, wherein said coating on said beads is selected from the group consisting of antibodies, antigens, hydrophobic coating materials, ligands and receptors.

34. The method of claim 32, comprising the step of transferring said beads from said sample vessel to a wash vessel and washing impurities from said beads prior to transferring to said eluting vessel.

35. The method of claim 32, further comprising the step of recovering said target component from said eluting agent in said eluting vessel.

36. The method of claim 32, further comprising the step of inserting a magnetizable probe into said sample vessel, magnetizing said probe to capture said beads, and retracting said probe and said beads from said sample vessel.

37. The method of claim 36, further comprising the step of transferring said probe and beads to said eluting vessel to elute said target component from said beads.

38. The method of claim 37, further comprising demagnetizing said probe to release said beads into said eluting agent.

39. The method of claim 38, further comprising magnetizing said probe after said eluting step to capture said beads from said eluting agent.

40. The method of claim 32, comprising providing a first magnetizable probe and a second magnetizable probe, said first and second probes being coupled to a support member, said support member being rotatable about an axis, wherein said sample contains a first amount of said beads and said eluting vessel contains a second amount of said beads, said method comprising the steps of:

moving said support member to a first position where said first probe is inserted into said sample vessel and said second probe is inserted in said eluting vessel;

magnetizing said first and second probes to capture said first amount of said beads in said sample vessel and said second amount of said beads in said eluting vessel, respectively;

raising said support member to remove said first and second probes from said sample vessel and said eluting vessel, respectively;

rotating said support member and lowering said support member to a second position where said first probe is inserted in said eluting vessel and said second probe is inserted in said sample vessel; and demagnetizing said probes to release said first amount of said beads in said eluting vessel and to release said second amount of said beads in said sample vessel.

41. The method of claim 32, subsequent to returning said beads to said sample vessel, said method comprising further contacting said liquid with the beads in said sample vessel, transferring said beads to said eluting vessel again, and eluting said target component from said beads to said eluting agent in said eluting vessel.

42. The method of claim 32, further comprising repeating at least three times in sequence said steps of contacting said liquid to said beads, said transferring said beads to an eluting vessel, eluting said target component into said eluting vessel, and returning said beads to said sample vessel.

43. A method of claim 32, further comprising repeating said contacting step, said step of transferring said beads to said eluting vessel, said eluting step and said returning step a predetermined number of times, and thereafter recovering said target component from said eluting vessel.

44. A method of recovering a denatured protein from a sample, said method comprising the steps of:

providing a solution containing said denatured protein from said sample;

contacting said solution with an amount of magnetically responsive beads, said beads having an outer surface having a specific binding affinity for native protein, said beads being contacted with said solution for sufficient time to bind said denatured protein to said beads;

recovering said beads from said solution, and eluting said denatured protein from said beads.

45. The method of claim 44, wherein said beads have a polymeric coating with pendant hydrophobic hydrocarbon groups.

46. The method of claim 44, wherein said beads have a polymeric coating with pendant hydrocarbon groups having about 18 carbon atoms.

* * * * *